(12) United States Patent
Meirelles et al.

(10) Patent No.: US 12,171,544 B2
(45) Date of Patent: Dec. 24, 2024

(54) MEDICAL IMAGING TOOTH DISPLACEMENT SYSTEMS AND METHODS

(71) Applicant: The Regents of the University of Michigan, Ann Arbor, MI (US)

(72) Inventors: Luiz Duarte Meirelles, Ann Arbor, MI (US); Rafael Amorim Cavalcanti De Siqueira, Ann Arbor, MI (US); Hom-Lay Wang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 598 days.

(21) Appl. No.: 17/441,585

(22) PCT Filed: Mar. 20, 2020

(86) PCT No.: PCT/US2020/023855
§ 371 (c)(1),
(2) Date: Sep. 21, 2021

(87) PCT Pub. No.: WO2020/198008
PCT Pub. Date: Oct. 1, 2020

(65) Prior Publication Data
US 2022/0192540 A1 Jun. 23, 2022

Related U.S. Application Data

(60) Provisional application No. 62/822,171, filed on Mar. 22, 2019.

(51) Int. Cl.
*A61B 5/11* (2006.01)
*A61B 1/24* (2006.01)
(Continued)

(52) U.S. Cl.
CPC .............. *A61B 5/1111* (2013.01); *A61B 1/24* (2013.01); *A61B 5/0053* (2013.01);
(Continued)

(58) Field of Classification Search
CPC ....... A61B 5/1111; A61B 1/24; A61B 5/0053; A61B 5/0062; A61B 5/0088;
(Continued)

(56) References Cited

U.S. PATENT DOCUMENTS

2008/0286712 A1 11/2008 Imgrund et al.
2010/0260405 A1 10/2010 Cinader, Jr.
(Continued)

FOREIGN PATENT DOCUMENTS

EP 3449862 3/2019

OTHER PUBLICATIONS

Goellner, M., Schmitt, J., Karl, M., Wichmann, M. and Holst, S., 2010. Photogrammetric measurement of initial tooth displacement under tensile force. Medical engineering & physics, 32(8), pp. 883-888.*
(Continued)

*Primary Examiner* — Zhitong Chen
(74) *Attorney, Agent, or Firm* — Jason R. Bond; Casimir Jones, S.C.

(57) ABSTRACT

The present disclosure relates to systems, computer programs, and methods employing oral cavity image capture for determining tooth displacement (e.g., for identifying patients with, or at risk for, periodontal disease). In certain embodiments, a medical imaging device or system (e.g., an intraoral scanner or other scanner) is employed to generate baseline and test scan images of at least one tooth, where the test scan is performed when the tooth in engaged with an opposing tooth in a chewing action, or is being pushed by an outside force, and the images are processed by a computer program to determine the amount of displacement of the tooth in at least one direction.

28 Claims, 19 Drawing Sheets

(51) Int. Cl.
A61B 5/00 (2006.01)
A61C 9/00 (2006.01)
G06T 7/00 (2017.01)

(52) U.S. Cl.
CPC .......... *A61B 5/0062* (2013.01); *A61B 5/0088* (2013.01); *A61B 5/7275* (2013.01); *A61C 9/0053* (2013.01); *G06T 7/0012* (2013.01); G06T 2207/30036 (2013.01)

(58) Field of Classification Search
CPC ... A61B 5/7275; A61B 5/6847; A61B 5/1122; A61B 5/1128; A61B 5/7282; A61C 9/0053; A61C 19/04; A61C 9/0046; G06T 7/0012; G06T 2207/30036
See application file for complete search history.

(56) References Cited

U.S. PATENT DOCUMENTS

| | | |
|---|---|---|
| 2016/0008096 A1 | 1/2016 | Wu et al. |
| 2016/0135925 A1* | 5/2016 | Mason .................... A61C 7/002 703/2 |
| 2016/0157967 A1 | 6/2016 | Kim et al. |
| 2018/0125610 A1 | 5/2018 | Carrier, Jr. et al. |
| 2018/0206940 A1 | 7/2018 | Kopelman et al. |
| 2019/0000592 A1 | 1/2019 | Cam et al. |
| 2019/0151046 A1* | 5/2019 | Kim ..................... A61C 9/0046 |

OTHER PUBLICATIONS

Yoshida, N., Koga, Y., Kobayashi, K., Yamada, Y. and Yoneda, T., 2000. A new method for qualitative and quantitative evaluation of tooth displacement under the application of orthodontic forces using magnetic sensors. Medical engineering & physics, 22(4), pp. 293-300.*

International Search Report and Written Opinion for PCT/US20/23855. Mailed Jun. 26, 2020. 17 pages.

Extended European Search Report for PCT/US2020023855. Mailed Jul. 28, 2022. 10 pages.

Burgett et al., A randomized trial of occlusal adjustment in the treatment of periodontitis patients. J Clin Periodontol. Jul. 1992;19(6):381-7.

Feldman et al., Interexaminer agreement in the measurement of periodontal disease. J Periodontal Res. Jan. 1982;17(1):80-9.

Ferris. Quantitative evaluation of tooth mobility following initial periodontal therapy. J Periodontol. May-Jun. 1966;37(3):190-7.

Fleszar et al., Tooth mobility and periodontal therapy. J Clin Periodontol. Dec. 1980;7(6):495-505.

Giargia et al., Tooth mobility and periodontal disease. J Clin Periodontol. Nov. 1997;24(11):785-95.

Hinterkausen et al., In vitro analysis of the initial tooth mobility in a novel optomechanical set-up. Med Eng Phys. Jan. 1998;20(1):40-9.

Ismail et al., Natural history of periodontal disease in adults: findings from the Tecumseh Periodontal Disease Study, 1959-87. J Dent Res. Feb. 1990;69(2):430-5.

Kawarizadeh et al., Experimental and numerical determination of initial tooth mobility and material properties of the periodontal ligament in rat molar specimens. Eur J Orthod. Dec. 2003;25(6):569-78.

Konermann et al., In vivo determination of tooth mobility after fixed orthodontic appliance therapy with a novel intraoral measurement device. Clin Oral Investig. May 2017;21(4):1283-1289.

Koo et al., A Guideline of Selecting and Reporting Intraclass Correlation Coefficients for Reliability Research. J Chiropr Med. Jun. 2016;15(2):155-63.

Mojon et al., Examiner agreement on periodontal indices during dental surveys of elders. J Clin Periodontol. Jan. 1996;23(1):56-9.

Muhlemann. Periodontometry, a method for measuring tooth mobility. Oral Surg Oral Med Oral Pathol. Oct. 1951;4(10):1220-33.

Nakago et al., Determination of the tooth mobility change during the orthodontic tooth movement studied by means of Periotest and MIMD (the mechanical impedance measuring device for the periodontal tissue). Am J Orthod Dentofacial Orthop. Jan. 1994;105(1):92-6.

Parfitt et al., Measurement of the physiological mobility of individual teeth in an axial direction. J Dent Res. May-Jun. 1960;39:608-18.

Pedersen et al., Tooth displacement analysed on human autopsy material by means of a strain gauge technique. Eur J Orthod. Feb. 1991;13(1):65-74.

Persson. Assessment of tooth mobility using small loads. II. Effect of oral hygiene procedures. J Clin Periodontol. Dec. 1980;7(6):506-15.

Ramfjord. The Periodontal Disease Index (PDI) J Periodontol. Nov.-Dec. 1967;38(6):Suppl:602-10.

Rateitschak. The Therapeutic Effect of Local Treatment on Periodontal Disease Assessed upon Evaluation of Different Diagnostic Criteria 1. Changes in Tooth Mobility. Journal Periodontology 1963;34:540-544.

Schulte et al., Periotest for measuring periodontal characteristics—Correlation with periodontal bone loss. Journal of Periodontal Research. 1992, 27(3), 184-190.

Tanaka et al., Longitudinal measurements of tooth mobility during orthodontic treatment using a periotest. Angle Orthod. Jan. 2005;75(1):101-5.

Wang et al., The influence of molar furcation involvement and mobility on future clinical periodontal attachment loss. J Periodontol. Jan. 1994;65(1):25-9.

Yoshida et al., A new method for qualitative and quantitative evaluation of tooth displacement under the application of orthodontic forces using magnetic sensors. Med Eng Phys. May 2000;22(4):293-300.

* cited by examiner

FIG. 9
A.
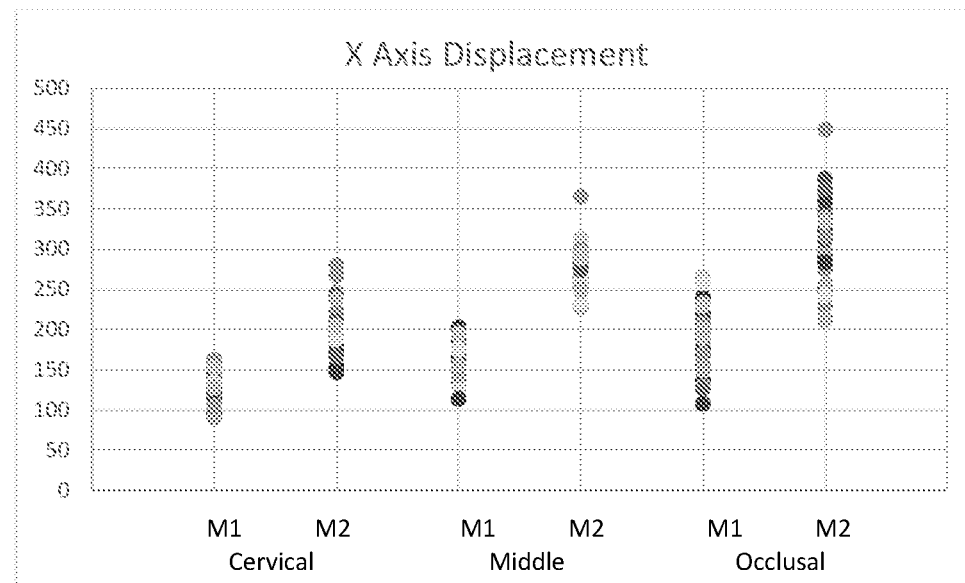
B.
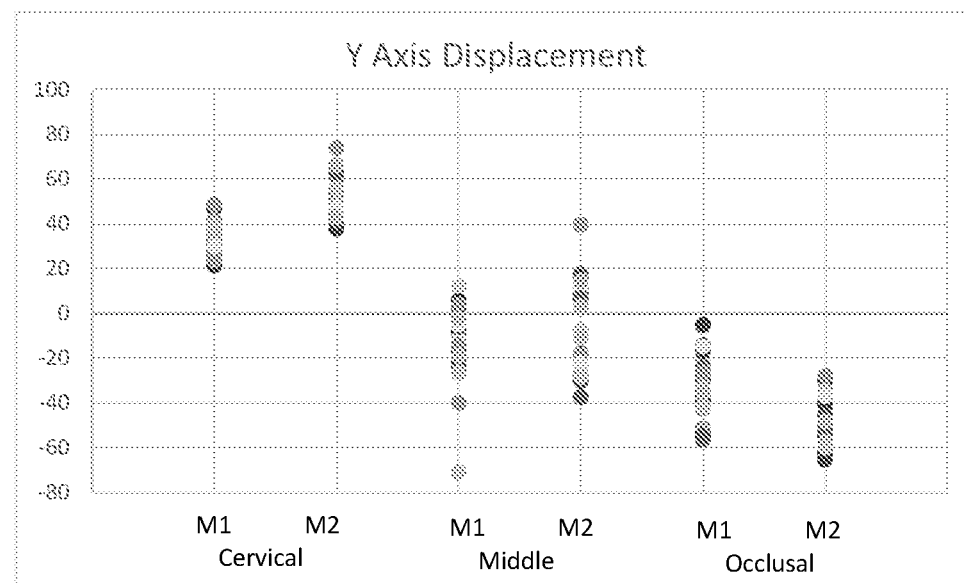

C.

| Axis | Points | % M1 | % M2 |
|---|---|---|---|
| X | C-M | 30.1% | 35.6% |
|   | C-O | 46.0% | 52.7% |
| Y | C-M | -141.8% | -111.7% |
|   | C-O | -195.9% | -194.3% |
| Z | C-M | 26.1% | 23.4% |
|   | C-O | 87.1% | 74.7% |

FIG. 12A-C
A. 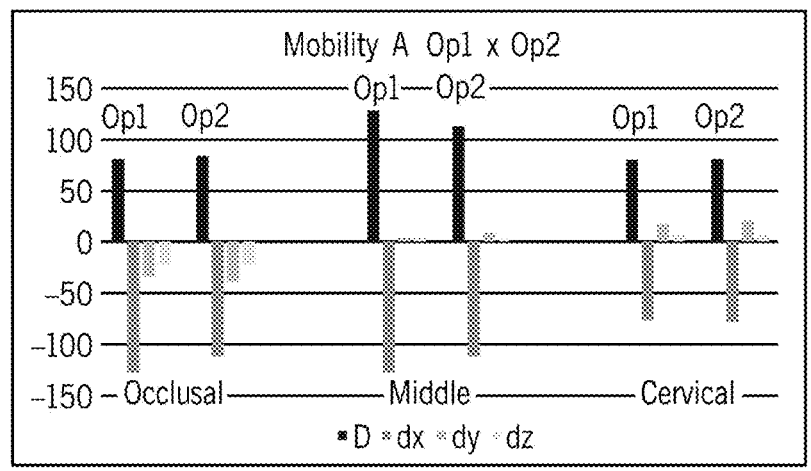
B. 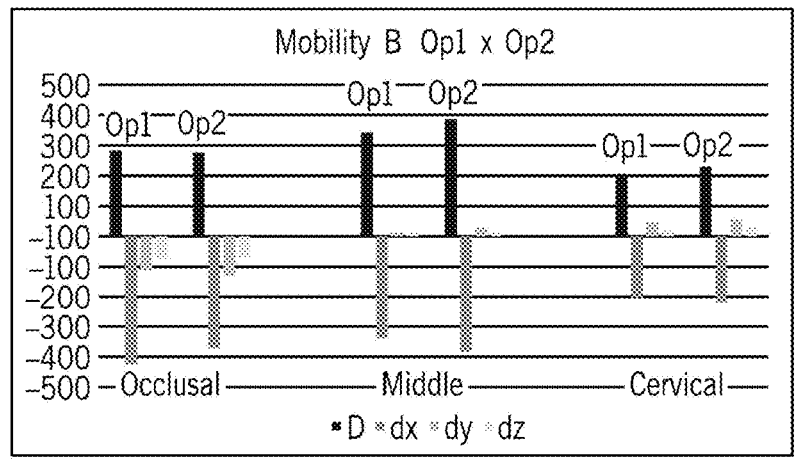
C. 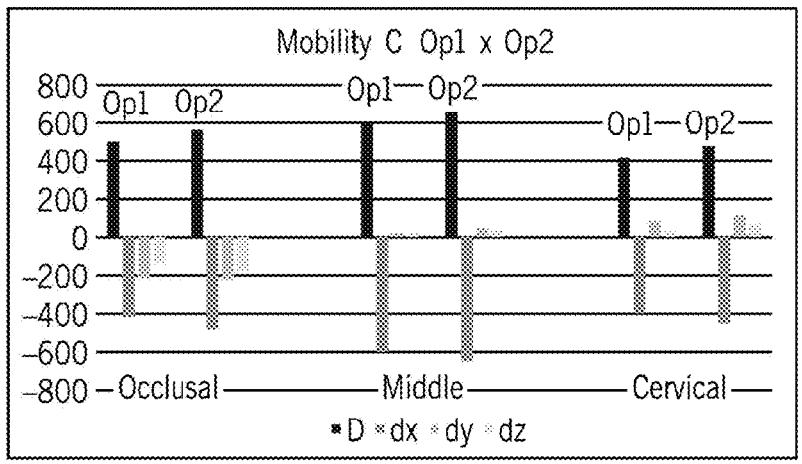

FIG. 15
A.
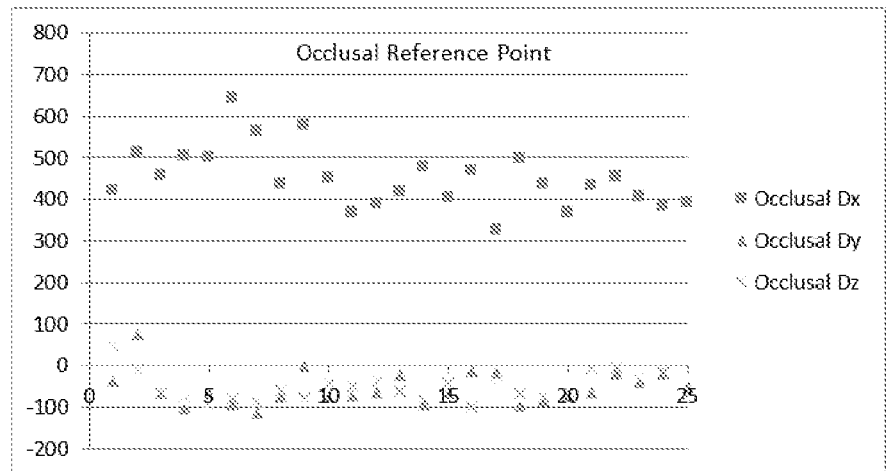
B.
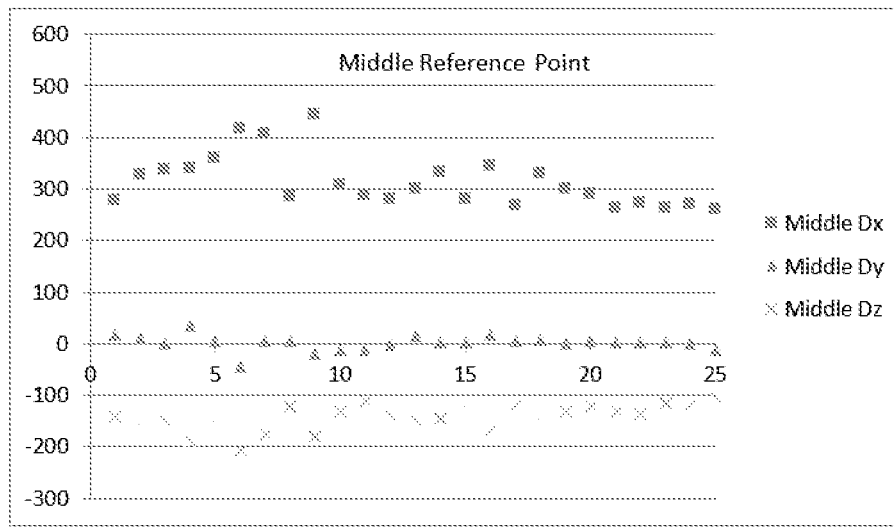
C.
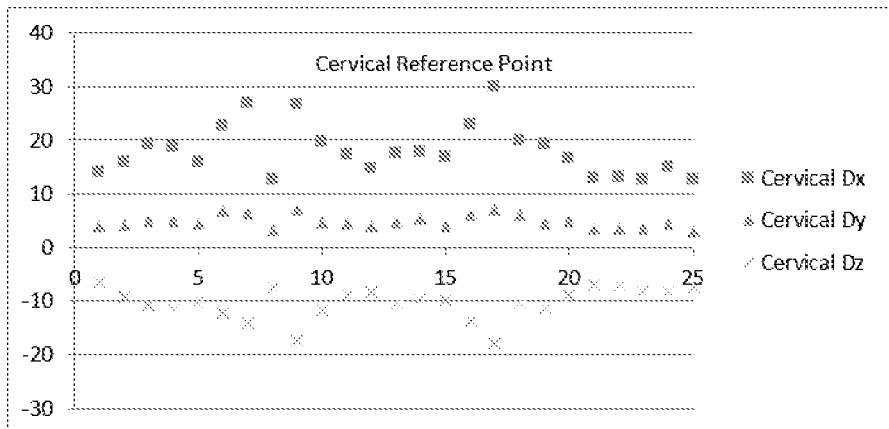

FIG. 16A-C
A.
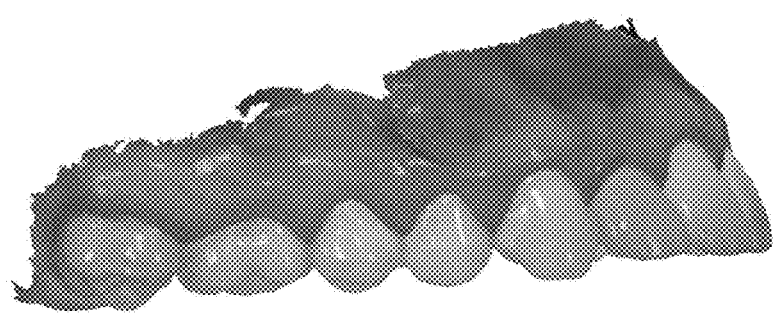
B.
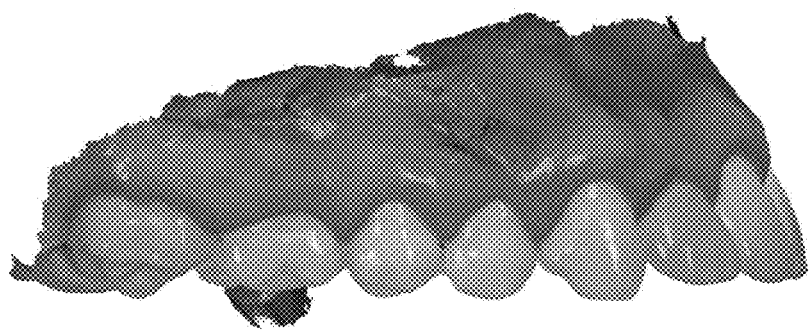
C.
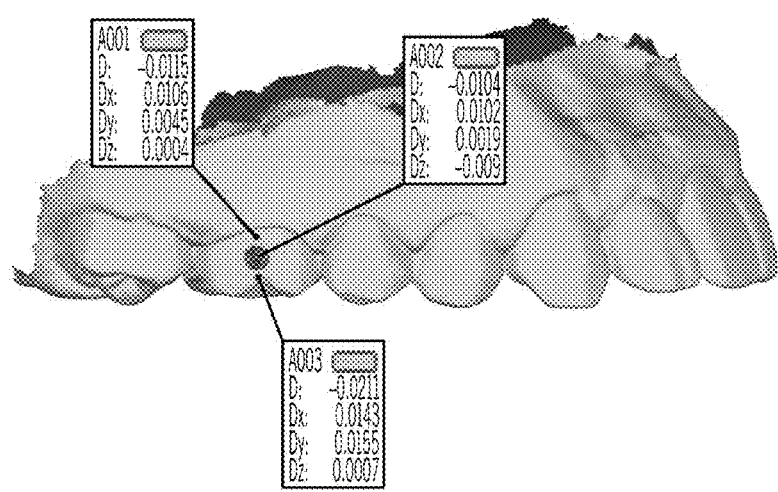

FIG. 17A-C
A.
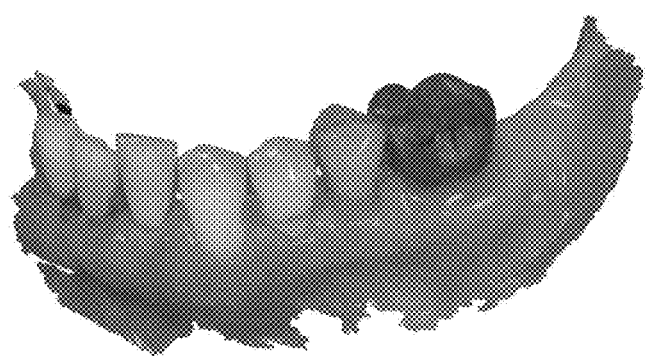
B.
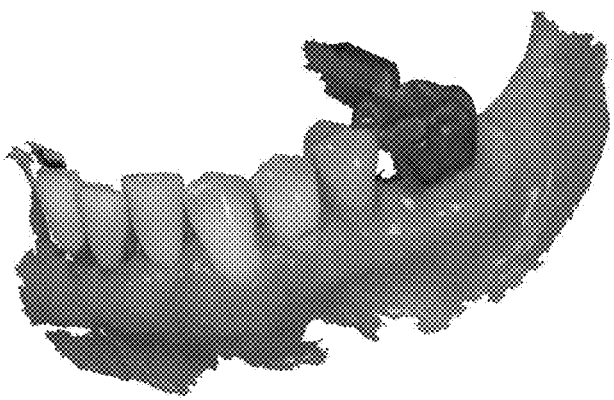
C.
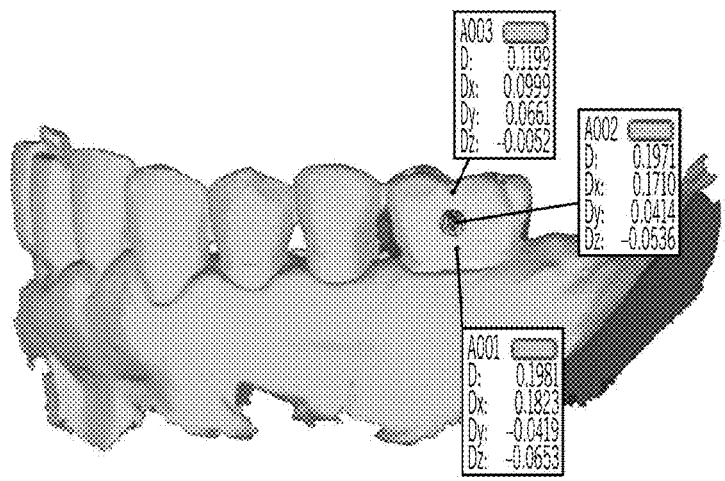

FIG. 18A-B
A.
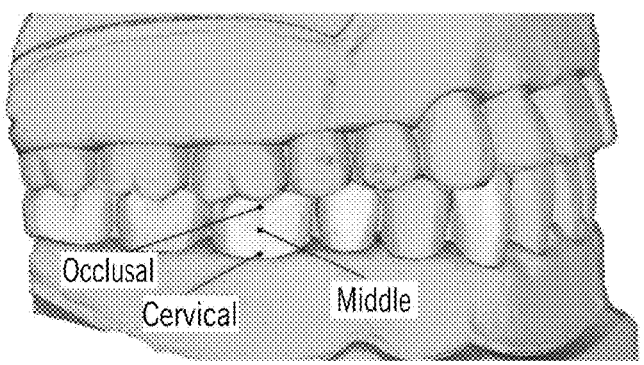
B.
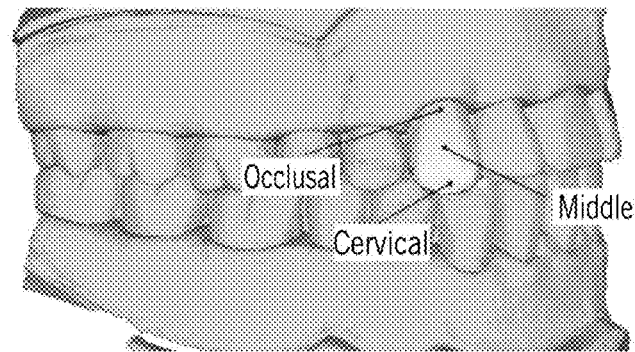

MEDICAL IMAGING TOOTH DISPLACEMENT SYSTEMS AND METHODS

The present application claims priority to U.S. Provisional application Ser. No. 62/822,171 filed Mar. 22, 2019, which is herein incorporated by reference in its entirety.

FIELD OF THE INVENTION

The present disclosure relates to systems, computer programs, and methods employing oral cavity image capture for determining tooth displacement (e.g., for identifying patients with, or at risk for, periodontitis). In certain embodiments, a medical imaging device or system (e.g., an intraoral scanner or other scanner) is employed to generate baseline and test scan images of at least one tooth, where the test scan is performed when the tooth is engaged with an opposing tooth in a chewing action, or is being pushed by an outside force, and the images are processed by a computer program to determine the amount of displacement of the tooth in at least one direction.

BACKGROUND

Tooth mobility is a routine evaluation performed to support the diagnosis and prognosis of periodontal disease. Miller proposed in 1938 a classification based on the displacement of the crown further categorized in groups according to horizontal and vertical thresholds (Miller S C. Textbook of Periodontia. Philadelphia: The blakiston Co.; 1938). Ramfjord in 1967 proposed a classification based on clinical aspects of tooth mobility, related to functional parameters, in attempt to overcome errors related to the lack of precision and accuracy of existing alternatives and to focus clinically relevant aspects (Ramfjord SP. The Periodontal Disease Index (PDI). J Periodontol 1967; 38: Supp1: 602-610; herein incorporated by reference). The limitation of tooth mobility outcome measures is not related to the classification itself. The major problem is the inherent subjective nature of the technique that requires the translation of a continuous variable to a categorical variable, grouping together a broad range of values in subgroups based on the perception of the examiner.

Clinical data investigating tooth prognosis demonstrated the potential of tooth mobility measurements to define the treatment outcome. Fleszar et al. demonstrated that sites with moderate (4-6 mm) and severe (7-12 mm) probing depths experienced clinical attachment loss associated to higher mobility compared to firm teeth after the first year following the periodontal theraphy (Fleszar et al., J Clin Periodontol 1980; 7:495-505). The relevance of initial mobility was highlighted in a 28 years retrospective study with a total of 325 patients (Ismail et al., J Dent Res 1990; 69:430-435). The patients with clinical attachment loss greater or equal 2 mm had tooth mobility at baseline and during the follow up, indicating that increase in tooth mobility is a risk factor for future attachment loss. Wang et al (1994) examined patients with furcation involvement after 8 years following periodontal therapy (Wang et al., J Periodontol 1994; 65:25-29). Molar teeth with mobility at baseline or 1 year had more attachment loss compared to molars without mobility, independent of furcation involvement. In contrast, sites treated with surgical and non-surgical periodontal therapy submitted to occlusal adjustment demonstrated gain in clinical attachment after 1 year independent of the initial mobility (Burgett et al., J Clin Periodontol 1992; 19:381-387).

Complex electronic and mechanical devices were developed in an attempt to generate accurate measurements of physiological and pathological displacements of tooth. Parfitt in 1960 developed an electronic device to measure the axial tooth displacement (Parfitt et al., J Dent Res 1960; 39:608-618). The author suggested that axial displacement would better relate to potential damage to all periodontal fibers, whereas bucco-lingual displacement was primarily related to the fibers in the cervical region. Muhelemann in 1951 developed a mechanical device to measure bucco-lingual displacement in response to different loads providing quantitative outcomes (Muhlemann H R. Periodontometry, Oral Surg Oral Med Oral Pathol 1951; 4:1220-1233). Clinical data using the Muhlemann device demonstrated a decrease in tooth mobility after non-surgical and surgical periodontal therapy (Ferris et al., J Periodontol 1966; 37:190-197. and Rateitschak, Journal Periodontology 1963; 34:540).

However, the clinical application of such experimental devices was limited due to the time required to set-up and the overall patient experience. The efforts to obtain reliable quantitative data on tooth mobility highlights the clinical relevance of such parameters. What is needed is a user-friendly concept based on objective measurements that will provide the opportunity to establish reliable oral health outcomes to define the need to treat and evaluate patient's prognosis.

SUMMARY OF THE INVENTION

The present disclosure relates to systems, computer programs, and methods employing oral cavity image capture for determining tooth displacement (e.g., for identifying patients with, or at risk for, periodontal disease). In certain embodiments, a medical imaging device or system (e.g., an intraoral scanner, computer-aided diagnosis system, or other scanner) is employed to generate baseline and test scan images of at least one tooth, where the test scan is performed when the tooth in engaged with an opposing tooth in a chewing action, or is being pushed by an outside force, and the images are processed by a computer program to determine the amount of displacement of the tooth in at least one direction.

In some embodiments, provided herein are methods of determining tooth displacement comprising: a) performing a first scan of at least a portion of the oral cavity of a subject using a medical imaging device or system (e.g., an intraoral scanner, computer-aided diagnosis system, or other scanner) to generate baseline scan data, wherein the baseline scan data comprises a baseline image of a first tooth (e.g., one or multiple teeth, such as 2 ... 5 ... 10 ... or all of the teeth in the oral cavity), and wherein the first scan is performed when the first tooth: i) is not engaged with an opposing tooth in a chewing action, and ii) is not being pushed by an outside force; b) performing a second scan (e.g., one or more scans on the same day or at different visits), of at least a portion of the oral cavity of the subject using a medical imaging device or system (e.g., an intraoral scanner or other scanner) to generate first test scan data, wherein the first test scan data comprises a first test image of the first tooth, wherein the second scan is performed when the first tooth is: i) engaged with the opposing tooth in a chewing action, or ii) is being pushed by an outside force; and c) processing the baseline scan data and the first test scan data with a processing system to thereby determine an amount of displacement of the first tooth in at least one direction, wherein the processing system comprises: i) a computer processor, and ii) non-transitory computer memory comprising one or more computer programs, wherein the one or more computer programs, in conjunction with the computer processor, is/are configured to align the baseline image and the first test image and calculate the amount of displacement of the first tooth (or teeth) in the at least one direction.

In some embodiments, the methods further comprise: performing a third scan of at least a portion of the oral cavity of said subject using a medical imaging device or system (e.g., an intraoral scanner, computer-aided diagnosis system, or other scanner) to generate second test scan data, wherein said second test scan data comprises a second test image of said first tooth, wherein said third scan is performed when said first tooth is: i) engaged with said opposing tooth in a chewing action, or ii) is being pushed by an outside force. In certain embodiments, the methods further comprise: processing said baseline scan data and said second test scan data with said processing system to thereby determine an amount of displacement of said first tooth in at least one direction. In additional embodiments, the methods further comprise: performing a fourth scan of at least a portion of said oral cavity of said subject using a medical imaging device or system (e.g., an intraoral scanner or other scanner) to generate third test scan data, wherein said third test scan data comprises a third test image of said first tooth, wherein said fourth scan is performed when said first tooth is: i) engaged with said opposing tooth in a chewing action, or ii) is being pushed by an outside force. In additional embodiments, the methods further comprise: processing said baseline scan data and said third test scan data with said processing system to thereby determine an amount of displacement of said first tooth in at least one direction. In certain embodiments, the one or more computer programs, in conjunction with the computer processor, is/are further configured to align the baseline image and the second test image and calculate the amount of displacement of the first tooth in the at least one direction. In some embodiments, the one or more computer programs, in conjunction with the computer processor, is/are further configured to align the baseline image and the third test image and calculate the amount of displacement of the first tooth in the at least one direction.

In certain embodiments, provided herein is non-transitory computer memory comprising one or more computer programs, wherein the one or more computer programs is/are configured to process baseline scan data and first test scan data with a processing system to thereby determine an amount of displacement of a first tooth (or multiple teeth) in at least one direction, wherein the baseline scan data is generated from a first scan of at least a portion of the oral cavity of a subject using a medical imaging device or system (e.g., an intraoral scanner or other scanner), wherein the baseline scan data comprises a baseline image of the first tooth (or multiple teeth, such as 2 . . . 5 . . . 10 . . . or all of the teeth in the oral cavity), wherein the first scan is performed when the first tooth (or multiple teeth): i) is not engaged with an opposing tooth in a chewing action, and ii) is not being pushed by an outside force, wherein the first test scan data is generated from a second scan of at least a portion of the oral cavity of the subject using a medical imaging device or system (e.g., an intraoral scanner or other scanner), wherein the first test scan data comprises a first test image of the first tooth (or multiple teeth), wherein the second scan is performed when the first tooth (or multiple teeth) is: i) engaged with the opposing tooth in a chewing action, or ii) is being pushed by an outside force; and wherein the one or more computer programs is/are further configured to align the baseline image and the first test image and calculate the amount of displacement of the first tooth (or multiple teeth) in the at least one direction.

In other embodiments, provided herein are processing systems comprising: a) a computer processor, and b) non-transitory computer memory comprising one or more computer programs, wherein the one or more computer programs, in conjunction with the computer processor, is/are configured to process baseline scan data and first test scan data with a processing system to thereby determine an amount of displacement of a first tooth (or multiple teeth) in at least one direction, wherein the baseline scan data is generated from a first scan of at least a portion of the oral cavity of a subject using a medical imaging device or system (e.g., an intraoral scanner, computer-aided diagnosis system, or other scanner), wherein the baseline scan data comprises a baseline image of the first tooth (or multiple teeth), wherein the first scan is performed when the first tooth: i) is not engaged with an opposing tooth in a chewing action, and ii) is not being pushed by an outside force, wherein the first test scan data is generated from a second scan of at least a portion of the oral cavity of the subject using a medical imaging device or system (e.g., an intraoral scanner or other scanner), wherein the first test scan data comprises a test image of the first tooth, wherein the second scan is performed when the first tooth (or multiple teeth) is: i) engaged with the opposing tooth (or multiple teeth) in a chewing action, or ii) is being pushed by an outside force; and wherein the one or more computer programs, in conjunction with the computer processor, is/are further configured to align the baseline image and the first test image and calculate the amount of displacement of the first tooth in the at least one direction.

In some embodiments, the one or more computer programs are further configured to process the baseline scan data and second scan data with a processing system to thereby determine an amount of displacement of said first tooth in at least one direction, wherein said second scan data is generated from a third scan of at least a portion of the oral cavity of said subject using a medical imaging device or system (e.g., an intraoral scanner or other scanner), wherein said second test scan data comprises a second test image of said first tooth, wherein said third scan is performed when said first tooth is: i) engaged with said opposing tooth in a chewing action, or ii) is being pushed by an outside force. In certain embodiments, the one or more computer programs are further configured to process the baseline scan data and third scan data with a processing system to thereby determine an amount of displacement of said first tooth in at least one direction, wherein said third scan data is generated from a fourth scan of at least a portion of the oral cavity of said subject using a medical imaging device or system (e.g., an intraoral scanner or other scanner), wherein said third test scan data comprises a third test image of said first tooth, wherein said fourth scan is performed when said first tooth is: i) engaged with said opposing tooth in a chewing action, or ii) is being pushed by an outside force. In certain embodiments, the one or more computer programs, in conjunction with the computer processor, is/are further configured to align the baseline image and the second test image and calculate the amount of displacement of the first tooth in the at least one direction. In some embodiments, the one or more computer programs, in conjunction with the computer processor, is/are further configured to align the baseline image and the third test image and calculate the amount of displacement of the first tooth in the at least one direction.

In particular embodiments, the non-transitory computer memory further comprises a database, wherein the database comprises a periodontal disease algorithm, and wherein the one or more computer programs is configured to apply the amount of displacement of the first tooth to the periodontal disease algorithm and determine if the subject has, or is at elevated risk for, periodontal disease. In further embodiments, the periodontal disease algorithm comprises an operation that finds periodontal disease is present in the subject if the amount of displacement of the first tooth in a generally horizontal direction is at least 0.05 millimeters (e.g., at least 0.05 . . . 0.1 . . . 0.5 . . . 1.0 . . . 1.5 . . . 2.5 . . . 4.0 . . . or a range of 0.1-4.0 millimeters). In other embodiments, the periodontal disease algorithm comprises an operation that finds periodontal disease (e.g., gingivitis or periodontitis) is present in the subject if the amount of displacement of the first tooth in a generally horizontal direction is at least 1.1 millimeters.

In some embodiments, provided herein are methods of scanning an oral cavity of a subject comprising: a) performing a first scan of at least a portion of the oral cavity of a subject using a medical imaging device or system (e.g., an intraoral scanner or other scanner) to generate baseline scan data, wherein the baseline scan data comprises a baseline image of a first tooth (or multiple teeth), and wherein the first scan is performed when the first tooth (or multiple teeth) is not being pushed by an outside force; b) pushing on the first tooth (e.g., with a finger, or rod, or portion of a dental tool, such as a mirror) to cause displacement of the tooth in at least one direction, and c) performing a second scan) of at least a portion of the oral cavity of the subject using a medical imaging device or system (e.g., an intraoral scanner or other scanner) to generate test scan data, wherein the test scan data comprises a test image of the first tooth, and wherein the second scan is performed when the first tooth is being pushed in step b).

In particular embodiments, the baseline scan data further comprises a first reference point image from a first location in the oral cavity, and wherein the test scan data further comprises a first corresponding reference point image from the first location in the oral cavity. In other embodiments, the one or more computer programs employ the first reference point image and the first corresponding reference point image to align the baseline image and the test image. In further embodiments, the baseline scan data further comprises a second reference point image (or third, fourth, fifth reference point image) from a second location (or third, fourth, fifth location) in the oral cavity, and wherein the test scan data further comprises a second (third, or fourth, or fifth) corresponding reference point image from the second (third, or forth, or fifth) location in the oral cavity.

In additional embodiments, the first tooth is being pushed by an outside force selected from the group consisting of: a human finger, a dental mirror, a rod, or any other suitable sized and suitable rigid implement to push on a tooth. In additional embodiments, the first tooth is a type of tooth selected from the group consisting of: cuspid, incisor, molar, premolar, and third molar. In other embodiments, the baseline image of the first tooth, and the test image of the first tooth, are both 3-D images.

In some embodiments, the first tooth is pushed in a general buccal direction. In other embodiments, the first tooth is pushed in a general lingual direction. In certain embodiments, the at least one direction is selected from the group consisting of: generally buccal, generally lingual, generally apical, generally coronal, generally mesial, and generally distal. In particular embodiments, the at least one direction is at least two different directions selected from the group consisting of: generally, buccal, generally lingual, generally apical, generally coronal, generally mesial, and generally distal. In further embodiments, the at least one direction is at least three different directions selected from the group consisting of: generally, buccal, generally lingual, generally apical, generally coronal, generally mesial, and generally distal.

In some embodiments, the amount of displacement of the first tooth is the amount of displacement of the crown of the first tooth. In other embodiments, the amount of displacement of the crown of the first tooth is the amount of displacement of at least one of the following: i) the cervical area of the crown, ii) the middle area of the crown, and iii) the occlusal area of the crown. In further embodiments, wherein the amount of displacement of the crown of the first tooth is the average amount of displacement of the cervical area, the middle area, and the occlusal area of the crown. In certain embodiments, a second tooth (or second, third, fourth, etc.) is pushed and scanned at, or about, the same time as the first tooth and images are processed as described above and herein.

In certain embodiments, the first tooth is being pushed by an outside force comprises at least 0.05 N of force applied to the first tooth. In particular embodiments, the first tooth is being pushed by an outside force comprises between 0.05 and 25 N of force (e.g., 0.05 . . . 1.5 . . . 3.5 . . . 5.0 . . . 10.0 . . . 17.0 . . . or 25 N) is applied to the first tooth.

In particular embodiments, the second scan is performed when the first tooth (or multiple teeth) is engaged with the opposing tooth (or multiple teeth) in a chewing action. In other embodiments, the second scan is performed when the first tooth is being pushed by an outside force. In additional embodiments, the subject is suspect of having periodontal disease. In certain embodiments, the first tooth (or teeth) is being pushed by opposing teeth (or tooth) during chewing by a force comprises between 1 and 25 N of force.

BRIEF DESCRIPTION OF THE FIGURES

FIG. 10 shows that different mobility was observed and reported in microns, in Example 1, along the cervical, middle and occlusal points. (**)=p<0.001, #=0.02, @=0.04, and the proportional change observed between the selected reference points, such as:

cervical-middle and cervical-occlusal in different axis, reported as percentage.

Figure 11:
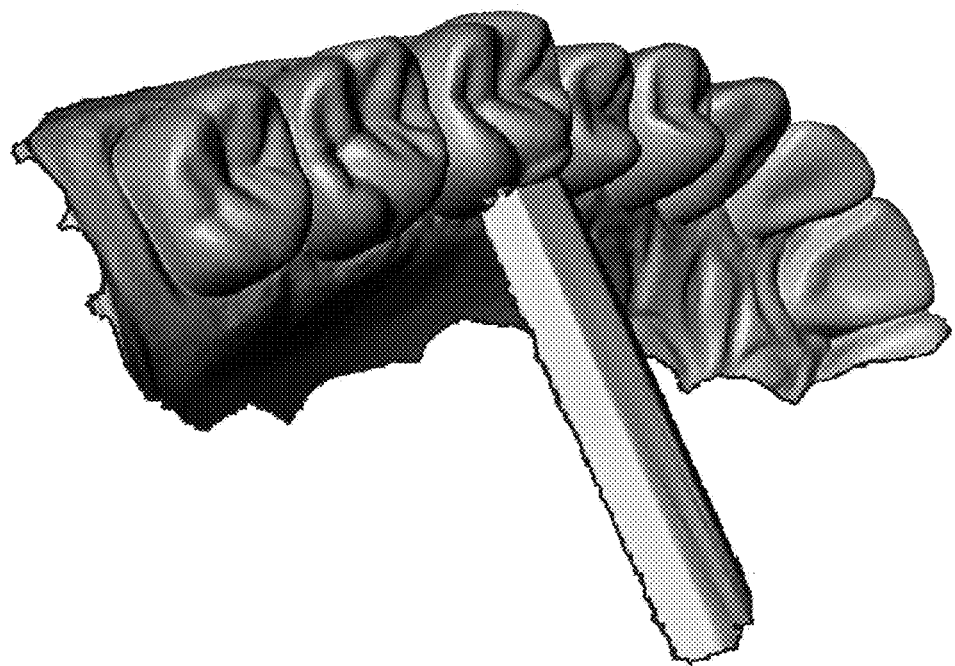

FIG. 11 shows an exemplary 3D scan of an intraoral cavity with a tooth being pushed by the end of the handle of a dental mirror.

FIG. 12 shows the results of Example 2 wherein two operators measured 3 different mobilities (A, B, and C) that were measured in microns at three different heights on the crown (occlusal, middle, and cervical) in the typodont. The three mobilities were generated by changing the level of attachment of the plastic tooth. FIG. 11A shows results for mobility A; FIG. 11B shows results for mobility B; and FIG. 11C shows results for mobility C.

Figure 13:
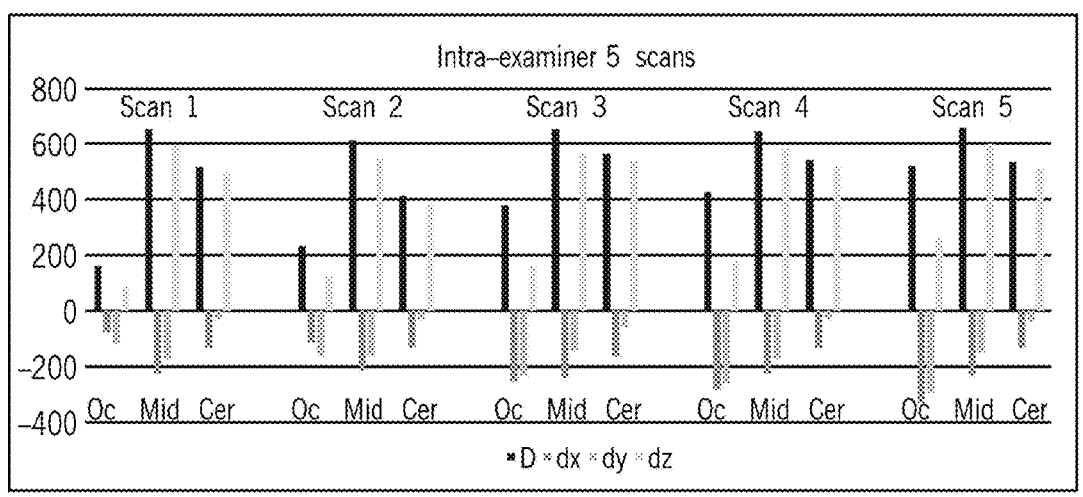

FIG. 13 shows the results of Example 2 where five measurements were obtained by a single operator at each of occlusal, middle, and cervical reference points.

Figure 14:
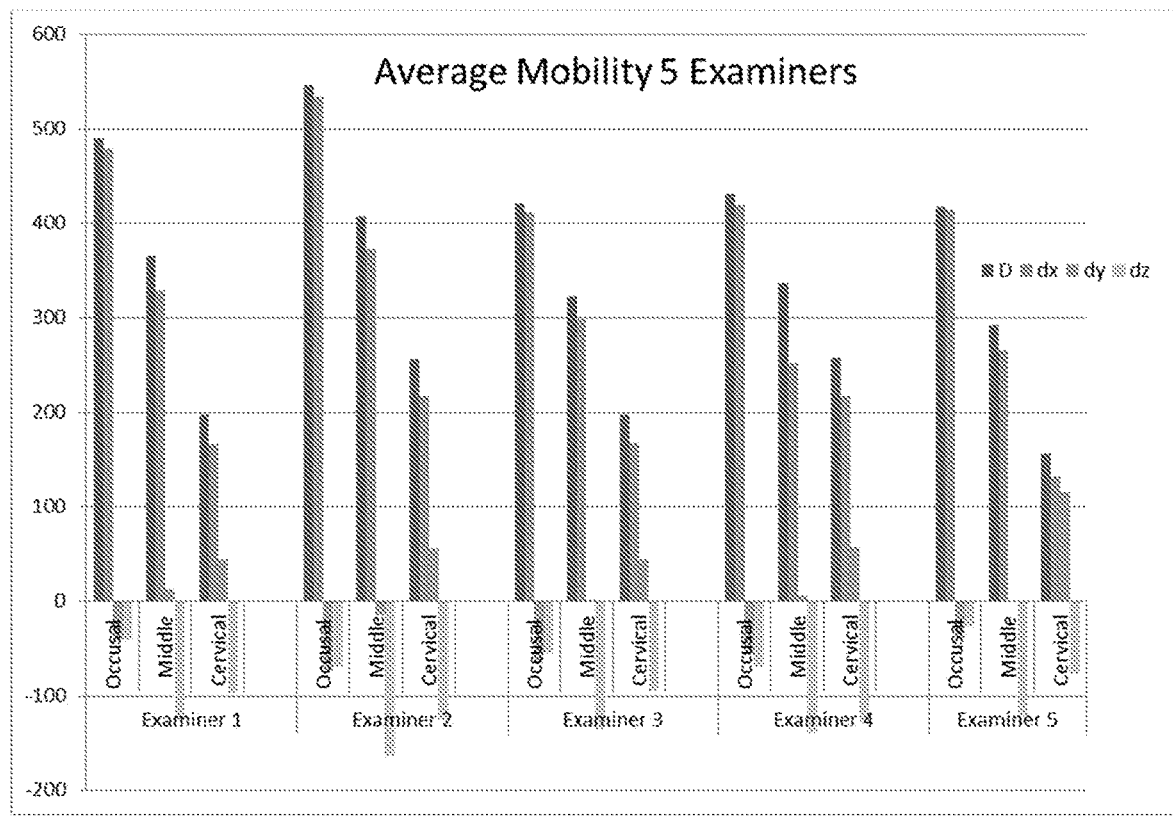

FIG. 14 shows the results in microns of Example 2 where 5 operators measured tooth mobility at each reference point occlusal, middle, and cervical.

FIG. 15 shows results of Example 2 where 5 operators employed 5 scans and measured tooth mobility in microns at occlusal (FIG. 15A), middle (FIG. 15B) and cervical (FIG. 15C) reference points.

FIG. 16 shows an exemplary tooth mobility evaluation in a patient without periodontal disease using a computer-aided diagnostic system, which includes: a) scan image of the mouth at baseline with no force applied; b) scan image of the mouth when a force is applied by the handle of a dental mirror on the first right maxillary tooth; c) tooth displacement values obtained after a) and b) were processed generating linear displacement in the three different axis in three reference points. Mean values calculated from three operators are represented in FIG. 16D. The overall displacement on the three reference points in all three axes below 15 microns indicates stable periodontium tissues compatible with absence of disease.

FIG. 17 shows an exemplary tooth mobility evaluation in a patient with periodontal disease using a computer-aided diagnostic system, which includes: a) scan image of the mouth at baseline with no force applied; b) scan image of the mouth when a force is applied by the handle of a dental mirror on the first mandibular left molar; c) tooth displacement values obtained after a) and b) were processed generating linear displacement in the three different axis at three reference points. Mean values calculated from three operators are represented in FIG. 17D. The displacement observed in the occlusal, middle and cervical points in the buccal direction (dx) ranging from 100 microns to 150 microns indicates unstable periodontium tissues compatible with the presence of disease.

FIG. 18 shows an exemplary tooth displacement in a typodont simulating the forces transmitted by an antagonist tooth during the movement of the mandible, such as chewing. Two scan files of tooth #30 and #6 were obtained without and with contact with the antagonist teeth. The two scan files were then processed and the 3D analysis used to establish the deviation at pre-determined points between the first and second scan. Three reference points at the tooth were chosen with the tool create annotations, providing the 3D deviation by linear deviation of each of the 3 axes (x, y, z) associated to a mandibular right first molar (FIG. 18A) and maxillary right canine (FIG. 18B). The mean values obtained by two operators in the cervical, middle and cervical reference points were determined in the three axes (x, y, z) (FIG. 18C). The data demonstrates a deviation to the lingual direction in the mandibular right first molar and to the buccal direction in tooth maxillary right canine during contact with the opposing teeth when a normal chewing contact is simulated.

Definitions

As used herein, the term "diagnosis" "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen or lifestyle change recommendations), and the like. In certain embodiments, a subject is diagnosed with periodontal disease supported on the tooth mobility methods and systems described herein.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject (e.g., a human at risk of periodontitis).

As used herein, the phrase "periodontal disease" also known as "gum disease," is a set of inflammatory conditions affecting the tissues surrounding the teeth. In its early stage, called gingivitis, the gums become swollen, red, and may bleed. In its more serious form, called periodontitis, the gums can pull away from the tooth, bone can be lost, and the teeth may loosen or fall out.

DETAILED DESCRIPTION OF THE INVENTION

The present disclosure relates to systems, computer programs, and methods employing oral cavity image capture for determining tooth displacement (e.g., for identifying patients with, or at risk for, periodontal disease). In certain embodiments, a medical imaging device or system (e.g., an intraoral scanner or other scanner) is employed to generate baseline and test scan images of at least one tooth, where the test scan is performed when the tooth in engaged with an opposing tooth in a chewing action, or is being pushed by an outside force, and the images are processed by a computer program to determine the amount of displacement of the tooth in at least one direction.

Provided herein are methods, systems, and software to determine tooth mobility based on intra-oral scanner measurements. In certain embodiments, such systems, software and methods provide reliable 3D quantitative oral health outcomes for physiological and non-physiological movements of the tooth. In some embodiments, provided herein are three-dimensional (3D) measuring techniques that utilize intra-oral scanners to capture the tooth position under different physiological and non-physiological function, providing: i) a systematic approach to collect reference points of the moving tooth or teeth, ii) a systematic approach to collect reference points of non-moving oral tissues, and iii) a tooth mobility calculation system which determine mobility of the tooth on the basis of the difference of the baseline output values compared to the outputs obtained during a single or multiple dental visits. In certain embodiments, the overall displacement of the tooth is provided as a quantitative outcome to be used for diagnosis, planning, assessing tooth prognosis, determining the need for intervention, and/or evaluating patients' progress with and without treatment.

The present disclosure provides, in certain embodiments, an accurate and reliable quantitative assessment of tooth displacement that can be used to measure tooth mobility by comparing different measurements using defined reference points of the moving tooth and non-moving tissues in the oral cavity. The measurement, in some embodiments, is obtained with an intra-oral scanner based measurements of the oral cavity structures generating accurate 3D mapping of the oral cavity structures which includes the tooth, or teeth, of interest, and the neighboring teeth. This provides a non-invasive technique that will collect data of tooth mobility without the need to intervene with invasive analog tools, such as periodontal or exploratory probes, minimizing the impact of the operator technique and experience on the outcome measure.

In certain embodiments, provided herein are tooth mobility assessment methods, that include: i) an integrated approach to determine reference points of the oral cavity structures, including the tooth of interest and neighboring tissues, ii) a minimum number of points at the tooth surface of interest to be considered to calculate tooth mobility at varying time points according to the outcome measurement of interest, iii) a minimum number of points or surfaces to be used as reference throughout the evaluations allowing accurate alignment of the oral cavity scans, iv) an internal check to indicate errors during measurement to inform the operator the need to redo the scan enabling scans comparison; and/or v) at least one main displacement outcome measurement along the 3-axis to be considered by the dental team during evaluation based on the disease or condition of interest. In certain embodiments, the tooth mobility data is incorporated into a subject's electronic oral and/or medical health records.

Image capturing sensors that will record the geometry of oral tissues based on passive or active light emission are known in the art. In general, the object is recorded as a single image or a video compiling data points of the region of interest to generate the three-dimensional digital reconstructions. Particular image capturing technologies available are: passive or active triangulation (AT), confocal laser scanning microscopy, accordion fringe interferometry (AFI), active wavefront sampling (AWS), and stereophotogrammetry. Exemplary commercial devices are displayed in Table 3.

TABLE 3

| SCANNER | TECHNOLOGY(IES) |
|---|---|
| PRIMEScan (Dentsply Sirona) | AT and CLSM |
| CEREC AC Omnicam (Dentsply Sirona) | AT and CLSM |
| CEREC AC BlueCam (Dentsply Sirona) | AT and CLSM |
| MIA 3D (Densys Ltd.) | AT stereophotogrammetry |
| DirectScan (HINT - ELS GMBH) | AT stereophotogrammetry |
| Virtuo Vivo (Dental Wings) | AT stereophotogrammetry |
| Condor (Condor Technologies) | AT stereophotogrammetry |
| iTero element (Align Technology) | CLSM |
| CS 3700 (Carestream Dental) | CLSM |
| Trios (3shape) | CLSM |
| Lythos (Digital Impressions, Ormco Corp) | AFI |
| Medit i500 (Medit) | AT |
| Midmark True definition (Midmark) | AWS |
| Planmeca Emerald S (Planmeca) | CLSM |
| Aadva IOS 200 (GC) | CLSM |
| ZFX IntraScan (Zfx GmbH) | CLSM and AFI |

EXAMPLES

The following examples are for purposes of illustration only and are not intended to limit the scope of the claims.

Example 1

Quantitative Tooth Mobility Evaluation Based on Intra-Oral Scanning

This Example employs an intraoral scanner to quantitatively test tooth mobility.

Material and Methods

Images Acquisition

Figure 1:
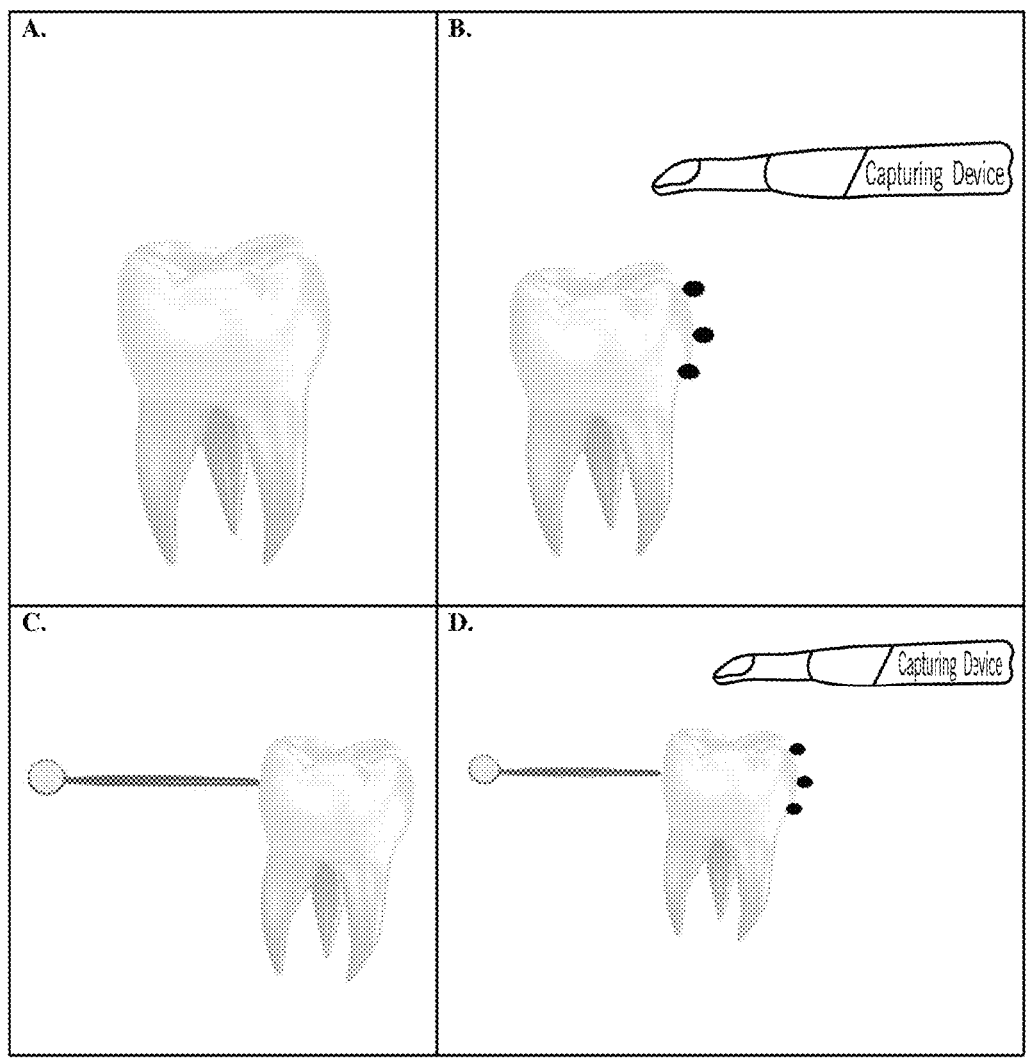
FIG. 1 shows an exemplary tooth mobility evaluation process, which includes: a) a representation of a tooth in the mouth at baseline with no displacement; b) a representation of a tooth in the mouth with no displacement at baseline with three reference points in the crown (occlusal, middle, and cervical) for tracking movement, and a medical imaging device or system (e.g., an intraoral scanner or other scanner) pointed at the tooth; c) a representation of a tooth in the mouth where displacement is observed via a dental mirror exerting force on the tooth; and d) a representation of a tooth in the mouth with a position different than the baseline. Displacement can be calculated, for example, on any one, or all three, reference points compared to baseline values.

The method in this Example is based on the 3D comparison of digital models obtained with an intra-oral scanner (Trios, 3hape, Denmark). A first digital impression of the typodont (SM-PVR-860, Columbia Dentoform, Long Island City, NY), as shown in FIG. 1, with its original configuration was obtained with the scanner and defined as the baseline. A series of digital impressions of the typodont was taken with the operators pushing the typodont's tooth to be analyzed into a buccal direction. The force was applied with the tip of the handle of a dental mirror placed in the lingual surface. The goal was to promote a movement in the tooth that simulates a dental mobility commonly associated with periodontitis.

A typodont model was used to simulate the clinical environment and two different degrees of tooth mobility were created by changing the tightness of the screw holding tooth #16. Each operator was asked to push the tooth into a buccal position to promote the movement, with the use of the handle of a dental mirror. An example of this is shown in the image in FIG. 2. The operator was asked also to hold the instrument at the final position of tooth movement while a second operator performed the scanning. Three experienced periodontists evaluated two mobility and repeated the measurements 10 times. The operators were asked to simulate the same force and direction used in a clinical setting. No instructions were provided to the operators regarding direction and magnitude of the force during the experiment.

Mobility Evaluation

Figure 3:
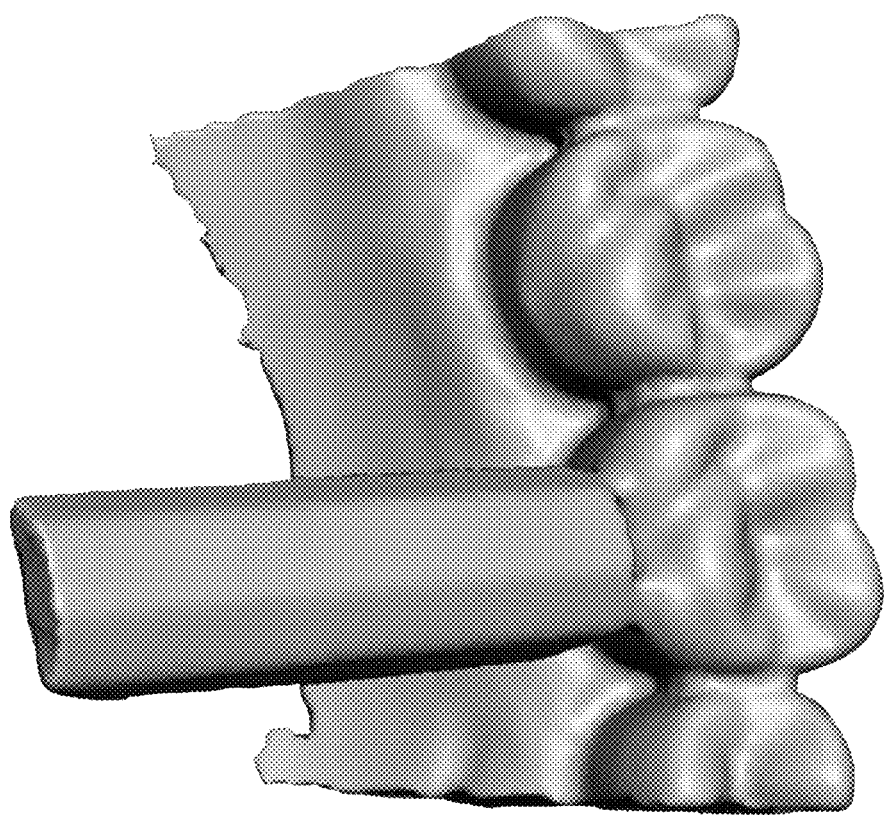
FIG. 3 shows an image of a typodont oral cavity model, shown with the handle of a dental mirror pushing on one of the teeth in the model.
Figure 4:
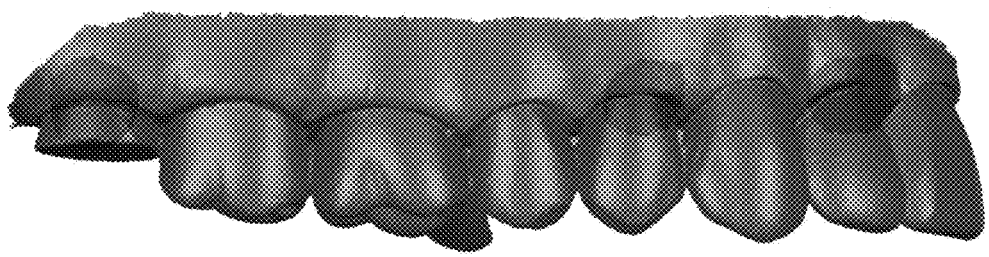
FIG. 4 shows an alignment of the two digital models obtained by intra-oral scanning from Example 1. Three coincident areas were employed as reference in each model for alignment.
Figure 5:
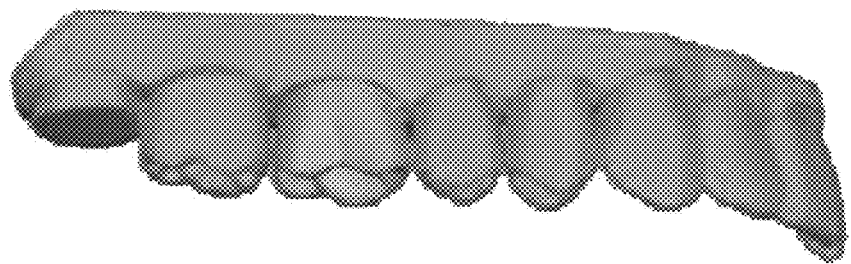
FIG. 5 shows a 3D comparison of the two digital models aligned. Different colors indicate amount of deviation between the models.
Figure 6:
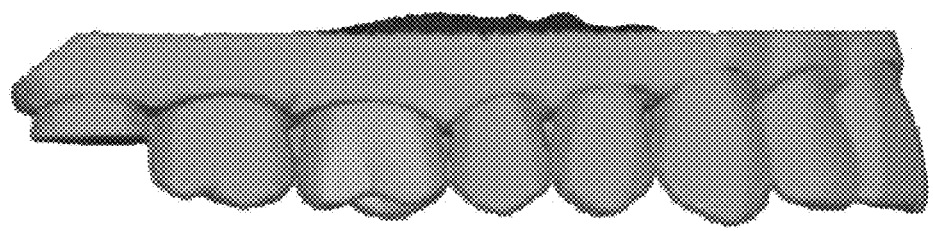
FIG. 6 shows how a grid tool and axis references were used to standardize image position for analysis.
Figure 7:
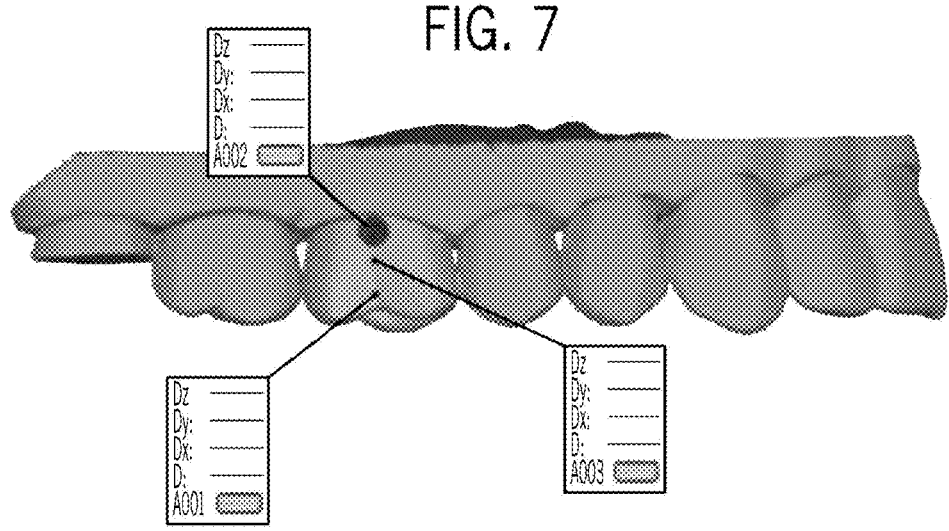
FIG. 7 shows three different reference points that were chosen to measure the linear movement in millimeters in the 3 different axis.

Digital impressions of the models were obtained with the scanner and the .stf files were exported from the software TRIOS (3shape, Denmark). The images were compared in the Geomagic Qualify software (3dsystems, North Carolina, USA). For the different evaluations, one baseline digital impression was obtained as reference and the different tested scenarios compared to generate the deviations at different pre-determined points in the crown (#16). The two models for each evaluation were then aligned using surfaces in the image not affected by the force applied to #16 (FIG. 3). Once the models were aligned and the fit confirmed, a 3D analysis tool was used to establish the deviation at pre-determined points between the reference and test models (FIG. 4). The image was positioned setting the buccal surface of the tooth in the screen and aligned 90° with the ground plane using regions not affected by the displacement of #16 (FIG. 5). For the displacement analysis, three reference points at the buccal surface of the tooth were chosen to determine by linear deviation in the 3 axis (x, y, z). The 3 areas chosen were in the cervical, middle and occlusal third of the tooth crown (FIG. 6). The linear measurements of the movement in the 3 different axes were collected for statistical analysis. The x, y and y axes represent the bucco-lingual, apical-coronal, and mesio-distal directions of the tooth anatomy. It was determined that a positive sign during the analysis represented a change to the buccal, apical, and mesial for the present evaluation, and a negative sign would relate to the lingual, coronal and distal, respectively (FIG. 7).

Statistical Analysis

The statistics analysis was performed to evaluate (1) reliability; (2) differences form mobility 1 and mobility 2, and (3) the variation in the different regions (cervical, middle, and occlusal). The reliability was analyzed by intraclass correlation coefficient (ICC). ICC estimates and their 95% confident intervals were calculated using SPSS statistical package version 24 (IBM, Chicago, IL). Based on the 95% confident interval of the ICC estimate, values less than 0.5, between 0.5 and 0.75, between 0.75 and 0.9, and greater than 0.90 are indicative of poor, moderate, good, and excellent reliability, respectevely[11]. Data from mobility 1 and 2 was analyzed by t-test for each examiner or pooled to support a comprehensive interpretation. Data analysis among the cervical, middle and occlusal points was performed by one-way analysis of variance (ANOVA). Significance level was set at 95%. Tooth displacement was calculated in microns (μm).

Results

Reliability

Table 1a and 1b shows the mean ±SD, inter-item correlation, Cronbach's alpha, Cronbach's alpha confidence interval CI (95%), and the F test for the ICC analysis.

TABLE 1A

| | | Mobility 1 | | | | | | |
| | | Cervical | | | | | Middle | |
| Axis | Examiners | Mean + SD | Inter-Item Correlation | C's α | CI (95%) | F Test | Mean + SD | Inter-Item Correlation |
| --- | --- | --- | --- | --- | --- | --- | --- | --- |
| x | 1 | 124.3 + 7.2 | 1-2 = .986 | .850 | .559-.959 | .000 | 178.9 + 17.3 | 1-2 = .961 |
|   | 2 | 132.4 + 25.7 | 1-3 = .933 |   |   |   | 149.5 + 21.2 | 1-3 = .929 |
|   | 3 | 132.7 + 13.3 | 2-3 = .901 |   |   |   | 178.4 + 15.0 | 2-3 = .953 |
| y | 1 | 32.8 + 4.7 | 1-2 = .944 | .931 | .798-.981 | .000 | −7.1 + 11.5 | 1-2 = .963 |
|   | 2 | 35.6 + 9.4 | 1-3 = .976 |   |   |   | −16.4 + 12.7 | 1-3 = .791 |
|   | 3 | 33.6 + 5.2 | 2-3 = .958 |   |   |   | −19.2 + 23.8 | 2-3 = .900 |
| z | 1 | −61.1 + 7.9 | 1-2 = .982 | .954 | .866-.988 | .000 | −46.2 + .17.8 | 1-2 = .859 |
|   |   | −59.4 + 12.9 | 1-3 = .931 |   |   |   | −41.7 + 12.5 | 1-3 = .969 |
|   | 3 | −63.0 + 7.9 | 2-3 = .950 |   |   |   | −47.8 + 15.3 | 2-3 = .913 |

| | | Mobility 1 | | | | | | |
| | | Middle | | | Occlusal | | | |
| Axis | Examiners | C's α | CI (95%) | F Test | Mean + SD | Inter-Item Correlation | C's α | CI (95%) | F Test |
| --- | --- | --- | --- | --- | --- | --- | --- | --- | --- |
| x | 1 | .972 | .918-.992 | .000 | 211.3 + 26.0 | 1-2 = .912 | .966 | .902-.991 | .000 |
|   | 2 |   |   |   | 145.2 + .20.1 | 1-3 = .960 |   |   |   |
|   | 3 |   |   |   | 221.2 + 22.1 | 2-3 = .885 |   |   |   |
| y | 1 | .891 | .681-.971 | .000 | −35.5 + .11.7 | 1-2 = .961 | .982 | .946-.995 | .000 |
|   | 2 |   |   |   | −.24.3 + 14.4 | 1-3 = .987 |   |   |   |
|   | 3 |   |   |   | −38.0 + 12.3 | 2-3 = .934 |   |   |   |
| z | 1 | .961 | .885-.989 | .000 | −17.8 + 21.0 | 1-2 = .963 | .942 | .829-.984 | .000 |
|   |   |   |   |   | −1.5 + 13.9 | 1-3 = .848 |   |   |   |
|   | 3 |   |   |   | −4.3 + 13.1 | 2-3 = .905 |   |   |   |

TABLE 1b

| | | Mobility 2 | | | | | | |
| --- | --- | --- | --- | --- | --- | --- | --- | --- |
| | | Cervical | | | | Middle | | |
| Axis | Examiners | Mean + SD | Inter-Item Correlation | C's α | CI (95%) | F Test | Mean + SD | Inter-Item Correlation |
| x | 1 | 192.0 + 33.7 | 1-2 = .848 | .949 | .852-.986 | .000 | 291.0 + 28.7 | 1-2 = .847 |
|   | 2 | 202.1 + 26.7 | 1-3 = .836 |      |           |      | 265.4 + 19.1 | 1-3 = .692 |
|   | 3 | 215.4 + 30.7 | 2-3 = .949 |      |           |      | 270.2 + 24.9 | 2-3 = .917 |
| y | 1 | 49.7 + 9.0   | 1-2 = .728 | .933 | .803-.982 | .000 | 10.5 + 15.6  | 1-2 = .843 |
|   | 2 | 52.7 + 8.4   | 1-3 = c.819|      |           |      | −10.4 + 21.2 | 1-3 = .838 |
|   | 3 | 51.3 + 8.6   | 2-3 = .928 |      |           |      | −18.0 + 14.1 | 2-3 = .856 |
| z | 1 | −100.9 + 18.1| 1-2 = .807 | .940 | .825-.984 | .000 | −98.8 + 33.0 | 1-2 = .860 |
|   | 2 | −102.3 + 14.1| 1-3 = .899 |      |           |      | −79.8 + 16.0 | 1-3 = .884 |
|   | 3 | —            | 2-3 = .881 |      |           |      | −60.4        | 2-3 = .882 |

| | | Mobility 2 | | | | | | |
| --- | --- | --- | --- | --- | --- | --- | --- | --- |
| | | Middle | | Occlusal | | | | |
| Axis | Examiners | C's α | CI (95%) | F Test | Mean + SD | Inter-Item Correlation | C's α | CI (95%) | F Test |
| x | 1 | .910 | .737-.976 | .000 | 362.8 + 36.1 | 1-2 = .857 | .937 | .816-.983 | .000 |
|   | 2 |      |           |      | 299.8 + 30.8 | 1-3 = .945 |      |           |      |
|   | 3 |      |           |      | 268.0 + 54.6 | 2-3 = .916 |      |           |      |
| y | 1 | .931 | .799-.981 | .000 | −54.0 + 8.8  | 1-2 = .953 | .976 | .928-993  | .000 |
|   | 2 |      |           |      | −45.1 + 7.6  | 1-3 = .928 |      |           |      |
|   | 3 |      |           |      | −45.9 + 10.1 | 2-3 = .968 |      |           |      |
| z | 1 | .892 | .685-.971 | .000 | −35.1 + 33.6 | 1-2 = .876 | .906 | .724-975  | .000 |
|   | 2 |      |           |      | −24.9 + 18.7 | 1-3 = .759 |      |           |      |
|   | 3 |      |           |      | −18.9        | 2-3 = .926 |      |           |      |

Figure 8:
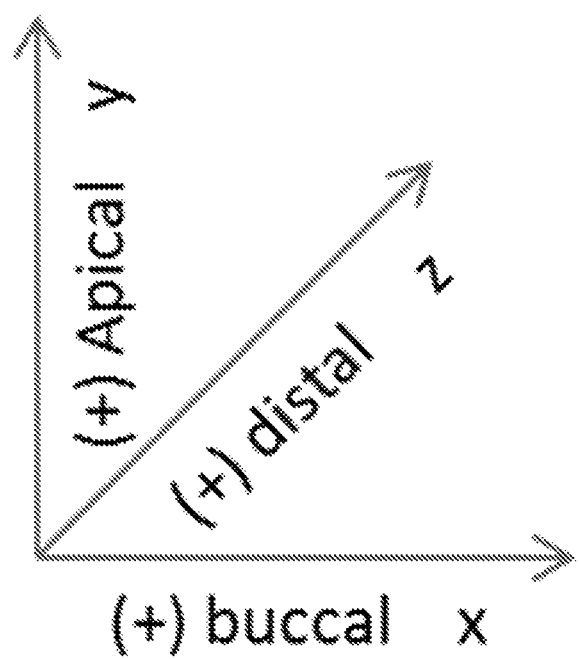
FIG. 8 shows the X, Y, Z axes direction in relation to the buccal-lingual, coronal-apical and mesio-distal planes.

The reliability of the technique is supported by the high Cronbach's alpha on the x, y and z axis for both mobility tested that scored above 0.9 in all groups, except for mobility 1 cervical x (0.850), mobility 1 middle y (0.891), and mobility 2 middle z (0.892). The analysis of the correlation between the examiners demonstrated excellent (above 0.90) or good (between 0.75 and 0.90) consistency of the measurements, except for mobility 1 cervical on they axis between examiners 1-2 (.728), and mobility 1 middle in the x axis between examiners 1-3 (0.692). A graphic representation of the data demonstrates the consistency of the measurements obtained in the different axis (FIG. 8).

Mobility 1×Mobility 2

Significant changes were detected in all axis at the three reference points comparing mobility 1 and 2 (Table 2).

TABLE 2

| Axis | Point | Δ M2 − M1 (μm) | Direction | p-value |
| --- | --- | --- | --- | --- |
| X | Cervical | 73 | Buccal | p < 0.001 |
|   | Middle | 107 | Buccal | p < 0.001 |
|   | Occlusal | 121 | Buccal | p < 0.001 |
| Y | Cervical | 17 | Apical | p < 0.001 |
|   | Middle | 8 | Apical | P = 0.002 |
|   | Occlusal | −16 | Coronal | p < 0.001 |
| Z | Cervical | −43 | Distal | p < 0.001 |
|   | Middle | −34 | Distal | p < 0.001 |
|   | Occlusal | −18 | Distal | p < 0.001 |

Change observed to mobility 1 and mobility 2 in the three axis and three points evaluated. The mean value and resulted magnitude Δ(m2−m1) and direction of the displacement is reported.

For the x axis, higher displacement of towards the buccal (P<0.001) was observed to mobility 2 compared to mobility 1 in the cervical, middle and occlusal points. The y axis showed a significant displacement to the apical at the cervical (P<0.001) and middle (p=0.002), whereas the displacement (P<0.001) at the occlusal was to the coronal direction, indicating a shift in resulting direction from mobility 1 to mobility 2 in the occlusal compared to the cervical and middle points. For the z axis, a displacement (P<0.001) at all points was observed to the distal.

Cervical x Middle X Occlusal

Figure 9:
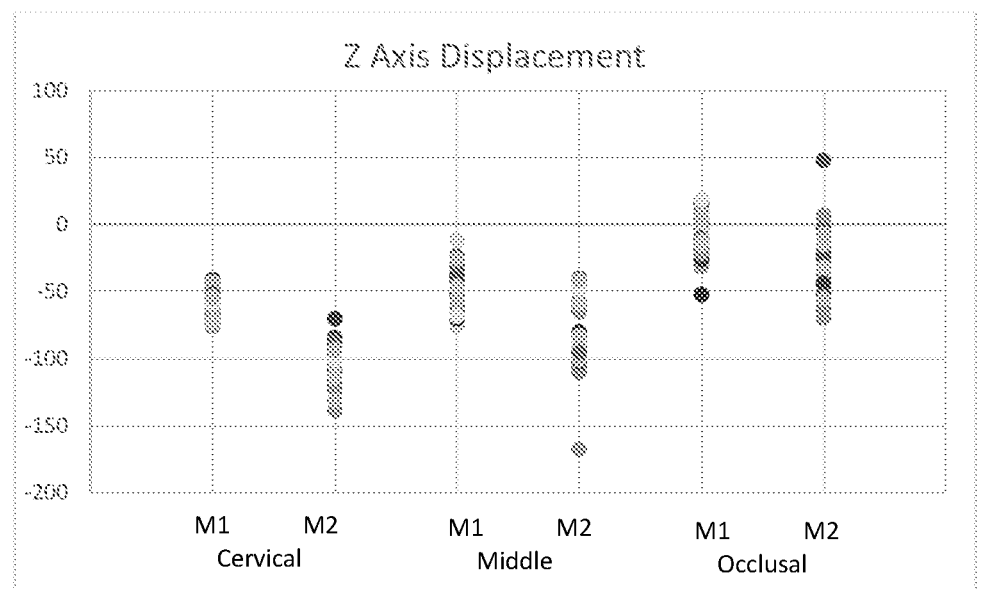
FIG. 9 shows a scatter plot of the data in microns obtained, in Example 1, at different axes showing a limited dispersion of the data in the different reference points for mobility 1 and 2. Value reported in μm, n=30.
Figure 10:
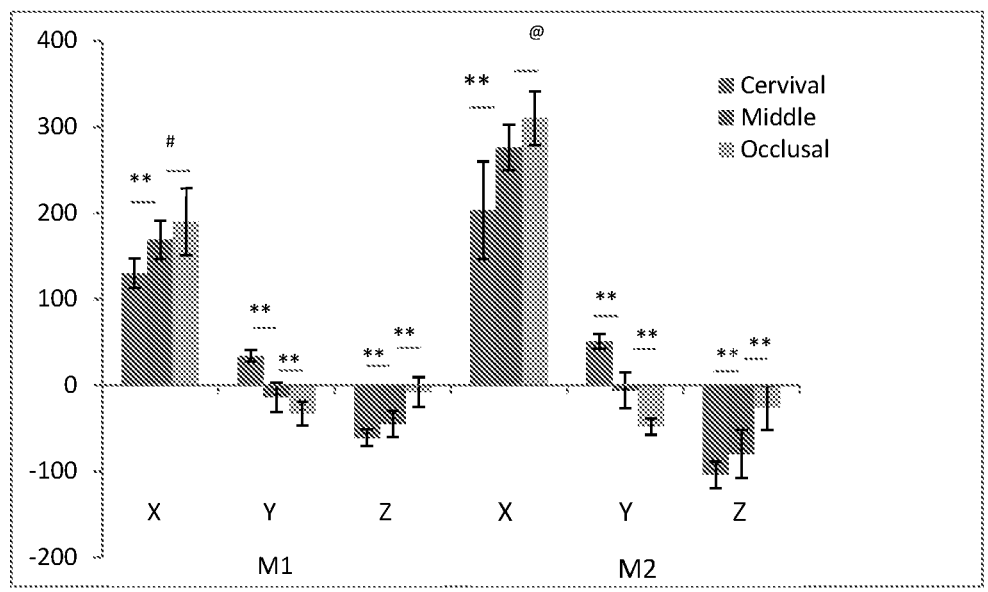

The data reporting the values calculated in the different points along the x, y, z axes is summarized in FIG. 9. The x axis demonstrated a gradual increase for both mobility in the middle compared to cervical (p<0.001), and for occlusal compared to middle for mobility 1 (p=0.02) and mobility 2 (p=0.04). For they axis, increase displacement to the coronal was observed to M compared to C (P<0.001) and 0 compared to M (P<0.001) for mobility 1 and 2. The z axis demonstrated higher displacement to the mesial for M compared to C (P<0.001) and 0 compared to M (P<0.001) for both mobility 1 and 2. Despite a significant difference in the values observed in mobility 1 compared to mobility 2, a similar change in percentages was observed between the cervical-middle and cervical-occlusal points, indicating a consistent movement in all points in all axes.

As shown in Table 1, excellent reliability was obtained testing different mobility as demonstrated by a high Cronbach's alpha above 0.9, and an inter-examiner correlation between 0.75>x<0.9 (good) or above 0.9 (excellent). Previous evaluation of mobility data was obtained based on a categorical data using $5^{12}$ or $2^{13}$ scores. The data was reported lower Cohen's k varying from poor (0.4) to moderate (0.6) between 2 examiners with 19 patients[13]. Higher values between 2 examiners based on the Pearson's correlation coefficient of 0.86 was obtained with the first set of 26 patients and 0.98 with 24 patients after recalibration[12]. The agreement of the data reported by the analysis of correlation should be done with cautious, since the coefficient shows the magnitude of the relationship, not the agreement. The reliability of the measurement depends on (1) the clarity of the criteria, (2) number of categories and (3) training of the examiners[13]. This Example demonstrates an objective measurement excluding the factors 1 and 2 that will generate an outcome restricted to the magnitude and the direction of the force applied by the operator.

Persson & Svensson (1980) in a clinical study associated greater tooth mobility measurements in periodontally compromised individuals, using a loading/sensing device. The apparatus utilized at the time was complex and presented several limitations like one dimensional recording possibility and no access to posterior teeth[14]. Schulte et al. (1992) examined the relationship between tooth mobility, assessed by means of the Periotest® (PVscore) and some clinical parameters of periodontal disease. The results showed that the percentage of bone loss was the parameter which was most highly correlated (r-=0.55) to the PVscore. Periotest instrument was also used in other studies, but a major limitation of this device is its restriction to only measure damping characteristics with a predefined frequency[15, 16]. Increased tooth mobility at baseline of periodontal treatment was one of the factors strongly associated with high levels of additional attachment loss during maintenance[4, 5]. Since tooth mobility could be a factor affecting severity, progression and therapeutic outcome of periodontal disease[3, 17], accurate measurement is important.

In this example, a significant difference in mobility from 8 μm in the y axis in the middle up to 121 μm in the x axis in the occlusal was successfully characterized. The displacement was significantly different within each examiner and with the data pooled (Table 2). This Examples provides an accurate alternative for the measurement that could be correlated to periodontal clinical parameters allowing a more comprehensive evaluation of periodontally compromised patients.

Different approaches to monitor tooth mobility and to understand the behavior of the PDL were reported in previous studies. The majority of the methods described were limited to in vitro application only, and in vivo studies are scarce[18-20]. Other studies implemented newly developed measurement systems in their investigations[21, 22]. Konermann et al. 2017[21] developed a new device for in vivo measurement of tooth mobility. The authors demonstrated precision and validity in clinical use of the device, however it requires the construction of an individual splint for the upper jaw of each patient for intraoral fixation of the device. The technique used in this Example, and in this application, does not require a splint. Moreover, the measurement performance demanded high precision from the investigator in terms of splint adaption and patient supervision to avoid unwanted movements potentially impacting the measurement results. This Example demonstrates a user-friendly non-invasive technique that can be performed by the dentist and the dental hygienist.

Example 2

Oral Health Quantitative Outcomes for Physiologic and Non-Physiologic Tooth Displacement This Example describes a method based on the 3D comparison of digital models obtained by digital impressions with an intra-oral scanner device (Trios, 3hape, Denmark). A first digital impression of the typodont on its original configuration was obtained and defined as the baseline. A second digital impression of the typodont was taken with the operator pushing the typodonts tooth to be analyzed, into a buccal direction. The force was applied with the tip of a dental mirror placed in the lingual surface. The goal was to promote a movement in the tooth that simulates a dental mobility commonly associated to periodontitis.

Digital impressions of the models were obtained and the stf files compared in Geomagic Qualify software (3dsystems, North Carolina, USA). For the different experiments, one baseline digital impression was obtained as reference and the different tested scenarios compared to generate the deviations at different pre-determined points in the crown. The two models were then aligned using the best-fit surface alignment tool of the software (FIG. B). Once the models are aligned and the fit confirmed, a 3D analysis is used to establish the deviation at pre-determined points between the reference and test models. The grid tool and axis were used as reference to standardize image position. Three reference points at the tooth were chosen with the tool create annotations, providing the 3D deviation by linear deviation of each of the 3 axis (x, y, z). The 3 areas chosen were in the half part of the buccal surface and in the cervical, middle and occlusal third of the tooth crown. The linear measurement of the movement in the 3 different axis was collected for statistical analysis.

Tooth Mobility Simulating Periodontitis

A series of tests was performed. A typodont model was used to simulate the clinical environment. Different mobility were created by changing the tightness of the screw holding tooth #16. All values reported in microns. Different scenarios were tested to evaluate the reliability:

Test 1
Intra-Examiner (2 Operators) with Three Different Mobilities

Two operators measured 3 different mobilities (A, B, and C) that were measured at three different heights on the crown (occlusal, middle, and cervical) in the typodont. The three mobilities were generated by changing the level of attachment of the plastic tooth. This was done by unscrewing the screw that holds the tooth, as one can change how firm the tooth is placed in the plastic model. This was done to mimic progression of the periodontal disease with increased mobility overtime. This was also done to show resolution measurement variations below 50 microns. Mean values (D, Dx, Dy, and Dz) reported by examiner (Op1 and Op2) at each reference point (occlusal, middle, and cervical). Results are shown in FIG. 11A-C.

Test 2
Intra-Examiner 5 Scans

Five measurements obtained by a single operator. Mean values (D, Dx, Dy, and Dz) reported by each scan at occlusal, middle, and cervical reference points, as shown in FIG. 12.

Test 3
A. 5 Inter-Examiner 5 Scans Mean Values 5 measurements obtained by 5 operators. Mean values (D, Dx, Dy, and Dz) reported by examiner at each reference point (occlusal (FIG. 13A), middle (FIG. 13B), and cervical (FIG. 13C)).

B. 5 Inter-examiner 5 scans scatter-plot 5 measurements obtained by 5 operators. Measurements: 1-5 operator 1; 6-10 operator 2; 11-15 operator 3; 16-20 operator 4; 21-25 operator 5. Values (Dx, Dy and Dz) calculated at occlusal (FIG. 14A), middle (FIG. 14B) and cervical (FIG. 14C) reference points.

Example 3

Computer-Aided Diagnosis System for Tooth Displacement in Patients without Periodontal Disease This Example is a clinical demonstration of the steps described in Example 1 using a computer-aided diagnosis system based on an intra-oral scanner device. A first digital impression of a patient without periodontal disease was obtained and defined as the baseline (16A). A second digital impression of the patient was taken with an operator pushing tooth #3 into a buccal direction (16B). The force was applied with a handle of a dental mirror placed in the lingual surface. The goal was to promote a movement in the tooth that simulates a dental mobility commonly associated to periodontitis.

Digital files of the first scan (baseline, (16A)) and of the second scan (pushed tooth, (16B)) were generated and the stf files compared in a comprehensive metrology software (Geomagic Control X (3D Systems). The two scan files were then processed and the 3D analysis used to establish the deviation at pre-determined points between the first and second scan. Three reference points at the tooth were chosen with the tool create annotations, providing the 3D deviation by linear deviation of each of the 3 axes (x, y, z) (16 C). Three reference points at the tooth were chosen with the tool create annotations, providing the 3D deviation by linear deviation of each of the 3 axes (x, y, z). Mean values calculated from three operators are represented in FIG. 16D. The overall displacement on the three reference points in all three axes below 15 microns indicates stable periodontium tissues compatible with absence of disease.

Example 4

Computer-Aided Diagnosis System for Tooth Displacement in Patients with Periodontal Disease This Example is a clinical demonstration of the steps described in Example 1 using a computer-aided diagnosis system based on an intra-oral scanner device. A first digital impression of a patient with periodontal disease was obtained and defined as the baseline (17A). A second digital impression of the patient was taken with an operator pushing tooth #20 into a buccal direction (17B). The force was applied with a handle of a dental mirror placed in the lingual surface. The goal was to promote a movement in the tooth that simulates a dental mobility commonly associated to periodontitis.

Digital files of the first scan (baseline, (17A)) and of the second scan (pushed tooth, (17 B)) were generated and the stf files compared in a comprehensive metrology software (Geomagic Control X (3D Systems). The two scan files were then processed and the 3D analysis used to establish the deviation at pre-determined points between the first and second scan. Three reference points at the tooth were chosen with the tool create annotations, providing the 3D deviation by linear deviation of each of the 3 axes (x, y, z) (17C). Mean values calculated from three operators are represented in FIG. 17D. The displacement observed in the occlusal, middle and cervical points in the buccal direction (dx) ranging from 100 microns to 150 microns indicates unstable periodontium tissues compatible with the presence of disease.

Example 5

Computer-Aided Diagnosis System for Tooth Displacement During Chewing

Figure 2:
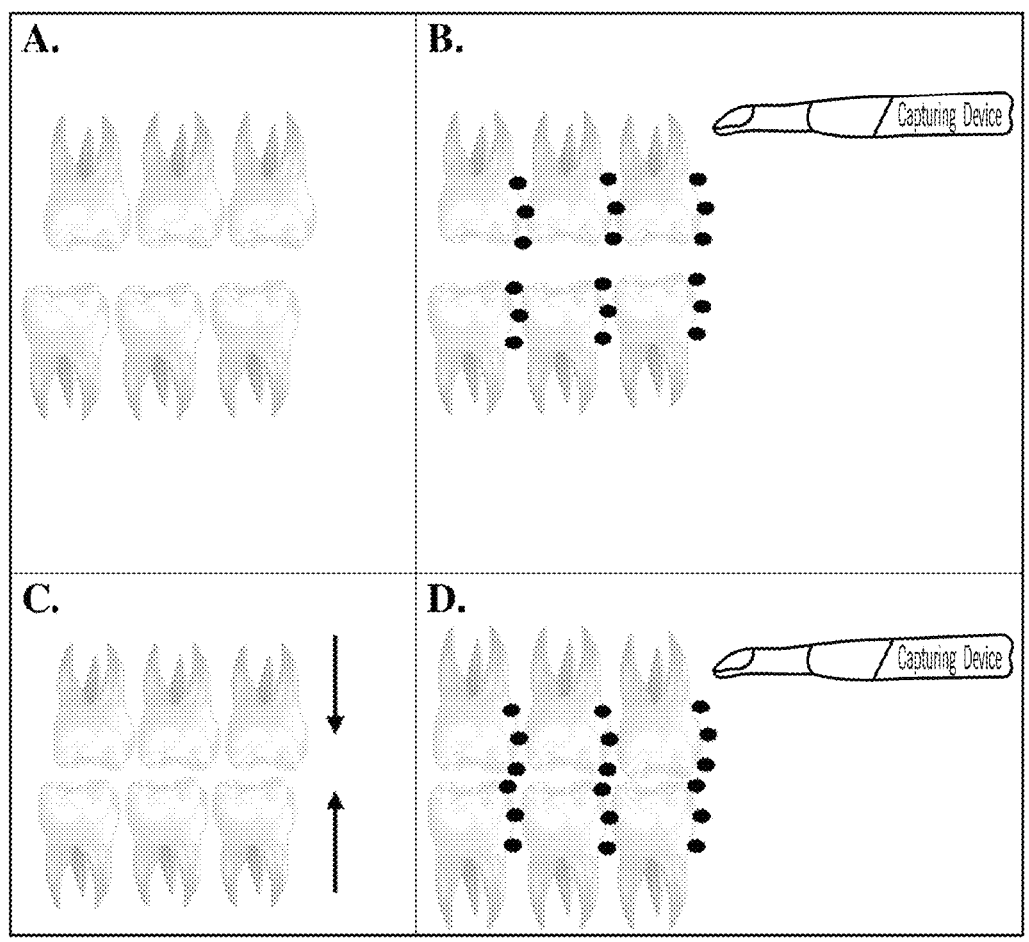
FIG. 2 shows an exemplary tooth or teeth mobility evaluation process, which includes: a) a representation of teeth in the mouth at baseline with no displacement; b) a representation of teeth in the mouth with no displacement at baseline with three reference points in the crown (occlusal, middle, and cervical) for tracking movement, and a medical imaging device or system (e.g., an intraoral scanner or other scanner) pointed at the teeth; c) a representation of teeth in the mouth where displacement is observed when the teeth are engaged with opposing teeth in a chewing action; and d) a representation of teeth in the mouth with a position different than the baseline due to the displacement promoted when teeth are engaged in a chewing action. Displacement can be calculated, for example, on any one, or all three, reference points compared to baseline values.

This Example is the final output obtained as described in FIG. 2. A first digital impression of a typodont with no displacement was aligned with a second scan with the mandibular right first molar and the maxillary right canine in a position different than the baseline due to the displacement promoted when teeth are engaged in a chewing action. Digital files of the first scan (no force from the antagonist tooth) and a second (with contact receiving force from the antagonist) were generated and the stf files compared in a comprehensive metrology software. The two scan files were then processed and the 3D analysis used to establish the deviation at pre-determined points between the first and second scan. Three reference points at the tooth were chosen with the tool create annotations, providing the 3D deviation by linear deviation of each of the 3 axes (x, y, z) associated to the mandibular right first molar (FIG. 18A) and maxillary right canine (FIG. 18B). The mean values obtained by three operators in the cervical, middle and cervical reference points were determined in in the three axes (x, y, z) (FIG. 18C). The data demonstrates a deviation to the lingual direction associated to the tooth located in the mandible and to the buccal direction in the teeth located in the maxilla during contact with the opposing teeth when a normal chewing contact is simulated.

REFERENCE

1. Miller S C. Textbook of Periodontia. Philadelphia: The blakiston Co.; 1938.
2. Ramfjord S P, J Periodontol 1967; 38:Supp1:602-610.
3. Fleszar et al., J Clin Periodontol 1980; 7:495-505.
4. Ismail et al., 1959-87. J Dent Res 1990; 69:430-435.
5. Wang et al., J Periodontol 1994; 65:25-29.
6. Burgett et al., J Clin Periodontol 1992; 19:381-387.
7. Parfitt G J, J Dent Res 1960; 39:608-618.
8. Muhlemann H R, Oral Surg Oral Med Oral Pathol 1951; 4:1220-1233.
9. Ferris R T, J Periodontol 1966; 37:190-197.
10. Rateitschak K H, Journal Periodontology 1963; 34:540.
11. Koo et al., J Chiropr Med 2016; 15:155-163.
12. Feldman et al., J Periodontal Res 1982; 17:80-89.
13. Mojon et al., J Clin Periodontol 1996; 23:56-59.
14. Persson R, J Clin Periodontol 1980; 7:506-515.
15. Tanaka et al., Angle Orthod 2005; 75:101-105.
16. Nakago et al., Am J Orthod Dentofacial Orthop 1994; 105:92-96.
17. Giargia et al., J Clin Periodontol 1997; 24:785-795.
18. Pedersen et al., Eur J Orthod 1991; 13:65-74.
19. Hinterkausen et al., Med Eng Phys 1998; 20:40-49.
20. Kawarizadeh et al., Eur J Orthod 2003; 25:569-578.
21. Konermann et al., Clin Oral Investig 2017; 21:1283-1289.
22. Yoshida et al., Med Eng Phys 2000; 22:293-300.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

We claim:

1. A method of determining tooth displacement comprising:
   a) performing a first scan of at least a portion of the oral cavity of a subject using an intraoral scanner to generate baseline scan data,
   wherein said baseline scan data comprises a baseline image of a first tooth comprising a crown, and
   wherein said first scan is performed when said first tooth:
      i) is not engaged with an opposing tooth in a chewing action, and ii) is not being pushed by an outside force;
   b) performing a second scan of at least a portion of said oral cavity of said subject, on the same day as the first scan, using an intraoral scanner to generate first test scan data,
   wherein said first test scan data comprises a first test image of said first tooth,
   wherein said second scan is performed when said first tooth is being pushed by an outside force; and
   c) processing said baseline scan data and said first test scan data with a processing system to thereby determine an amount of displacement of the occlusal or middle area of said crown of said first tooth in at least one direction, wherein said processing system comprises:
      i) a computer processor, and
      ii) non-transitory computer memory comprising one or more computer programs, wherein said one or more computer programs, in conjunction with said computer processor, is/are configured to align said baseline image and said first test image and calculate said amount of displacement of said occlusal or middle area of said crown of said first tooth in said at least one direction,
   wherein said amount of displacement of said occlusal or middle area of said crown of said first tooth in a general buccal or general lingual direction is at least 0.1 millimeters (100 microns),
   wherein said processing system further comprises a display component or is linked to a display component, and
   wherein the method further comprises: d) reporting that said subject has periodontal disease on said display component.

2. The method of claim 1, further comprising: performing a third scan of at least a portion of said oral cavity of said subject using an intraoral scanner to generate second test scan data, wherein said second test scan data comprises a second test image of said first tooth, wherein said third scan is performed when said first tooth is: i) engaged with said opposing tooth in a chewing action, or ii) is being pushed by an outside force.

3. The method of claim 2, further comprising: processing said baseline scan data and said second test scan data with said processing system to thereby determine an amount of displacement of said first tooth in at least one direction.

4. The method of claim 3, further comprising: performing a fourth scan of at least a portion of said oral cavity of said subject using an intraoral scanner to generate third test scan data, wherein said third test scan data comprises a third test image of said first tooth, wherein said fourth scan is performed when said first tooth is: i) engaged with said opposing tooth in a chewing action, or ii) is being pushed by an outside force.

5. The method of claim 4, further comprising: processing said baseline scan data and said third test scan data with said processing system to thereby determine an amount of displacement of said first tooth in at least one direction.

6. The method of claim 1, wherein said baseline scan data further comprises a first reference point image from a first location in said oral cavity, and wherein said first test scan data further comprises a first corresponding reference point image from said first location in said oral cavity.

7. The method of claim 6, wherein said one or more computer programs employ said first reference point image and said first corresponding reference point image to align said baseline image and said first test image.

8. The method of claim 7, wherein said baseline scan data further comprises a second reference point image from a second location in said oral cavity, and wherein said first test scan data further comprises a second corresponding reference point image from said second location in said oral cavity.

9. The method of claim 1, wherein said first tooth is being pushed by an outside force selected from the group consisting of: a human finger, a dental mirror, and a rod.

10. The method of claim 1, wherein said first tooth is a type of tooth selected from the group consisting of: cuspid, incisor, molar, premolar, and third molar.

11. The method of claim 1, wherein said baseline image of said first tooth, and said test image of said first tooth, are both 3-D images.

12. The method of claim 1, wherein said first tooth is pushed in a general buccal direction.

13. The method of claim 1, wherein said first tooth is pushed in a general lingual direction.

14. The method of claim 1, wherein said first tooth is being pushed by an outside force comprises at least 0.05 N of force applied to said first tooth.

15. The method of claim 1, wherein said first tooth is being pushed by an outside force comprises between 0.05 and 25 N of force is applied to said first tooth.

16. A processing system comprising:
   a) a computer processor,
   b) non-transitory computer memory comprising one or more computer programs, wherein said one or more computer programs, in conjunction with said computer processor, is/are configured to process baseline scan data and first test scan data with a processing system to thereby determine an amount of displacement of a first tooth comprising a crown in at least one direction,
   wherein said baseline scan data is generated from a first scan of at least a portion of the oral cavity of a subject using an intraoral scanner,
   wherein said baseline scan data comprises a baseline image of said first tooth,
   wherein said first scan is performed when said first tooth:
      i) is not engaged with an opposing tooth in a chewing action, and ii) is not being pushed by an outside force,
   wherein said first test scan data is generated from a second scan, on the same day as the first scan, of at least a portion of said oral cavity of said subject using an intraoral scanner,
   wherein said first test scan data comprises a first test image of said first tooth,
   wherein said second scan is performed when said first tooth is being pushed by an outside force;

wherein said one or more computer programs, in conjunction with said computer processor, is/are further configured to align said baseline image and said first test image and calculate said amount of displacement of the occlusal or middle area of said crown of said first tooth in said at least one direction, wherein said non-transitory computer memory further comprises a database, wherein said database comprises a periodontal disease algorithm, and wherein said one or more computer programs is configured to apply said amount of displacement of said occlusal or middle area of said crown of said first tooth to said periodontal disease algorithm and determine if said subject has, or is at elevated risk for, periodontal disease, and wherein said periodontal disease algorithm comprises an operation that finds periodontal disease is present in said subject when said amount of displacement of said occlusal or middle area of said crown of said first tooth in a general buccal or general lingual direction is at least 0.1 millimeters (100 microns), and c) a display component that reports said subject has said periodontal disease.

17. The system of claim 16, wherein the one or more computer programs are further configured to process the baseline scan data and second scan data with a processing system to thereby determine an amount of displacement of said first tooth in at least one direction, wherein said second scan data is generated from a third scan of at least a portion of the oral cavity of said subject using an intraoral scanner, wherein said second test scan data comprises a second test image of said first tooth, wherein said third scan is performed when said first tooth is: i) engaged with said opposing tooth in a chewing action, or ii) is being pushed by an outside force.

18. The system of claim 17, wherein the one or more computer programs are further configured to process the baseline scan data and third scan data with a processing system to thereby determine an amount of displacement of said first tooth in at least one direction, wherein said third scan data is generated from a fourth scan of at least a portion of the oral cavity of said subject using an intraoral scanner, wherein said third test scan data comprises a third test image of said first tooth, wherein said fourth scan is performed when said first tooth is: i) engaged with said opposing tooth in a chewing action, or ii) is being pushed by an outside force.

19. The system of claim 16, wherein said baseline scan data further comprises a first reference point image from a first location in said oral cavity, and wherein said first test scan data further comprises a first corresponding reference point image from said first location in said oral cavity.

20. The system of claim 19, wherein said one or more computer programs is further configured to employ said first reference point image and said first corresponding reference point image to align said baseline image and said first test image.

21. The system of claim 20, wherein said baseline scan data further comprises a second reference point image from a second location in said oral cavity, and wherein said first test scan data further comprises a second corresponding reference point image from said second location in said oral cavity.

22. The system of claim 16, wherein said first tooth is being pushed by an outside force selected from the group consisting of: a human finger, a dental mirror, and a rod.

23. The system of claim 16, wherein said first tooth is a type of tooth selected from the group consisting of: cuspid, incisor, molar, premolar, and third molar.

24. The system of claim 16, wherein said baseline image of said first tooth, and said test image of said first tooth, are both 3-D images.

25. The system of claim 16, wherein said first tooth is pushed in a general buccal direction when said first test scan data is generated.

26. The system of claim 16, wherein said first tooth is pushed in a general lingual direction when said first test scan data is generated.

27. The system of claim 16, wherein said first tooth is being pushed by an outside force comprises at least 0.05 N of force applied to said first tooth when said first test scan data is generated.

28. The system of claim 16, wherein said first tooth is being pushed by an outside force comprises between 0.05 and 25 N of force applied to said first tooth when said first test data is generated.

* * * * *